(12) United States Patent
Kilburn et al.

(10) Patent No.: US 8,138,342 B2
(45) Date of Patent: Mar. 20, 2012

(54) 11β-HYDROXYSTEROID DEHYDROGENASE TYPE 1 ACTIVE SPIRO COMPOUNDS

(75) Inventors: John Paul Kilburn, Haslev (DK); Henrik Sune Andersen, Lyngby (DK); Gita Camilla Tejlgaard Kampen, Nærum (DK)

(73) Assignee: High Point Pharmacueticals, LLC, High Point, NC (US)

( * ) Notice: Subject to any disclaimer, the term of this patent is extended or adjusted under 35 U.S.C. 154(b) by 756 days.

(21) Appl. No.: 11/665,103

(22) PCT Filed: Oct. 12, 2005

(86) PCT No.: PCT/EP2005/055181
§ 371 (c)(1),
(2), (4) Date: Dec. 23, 2008

(87) PCT Pub. No.: WO2006/040329
PCT Pub. Date: Apr. 20, 2006

(65) Prior Publication Data
US 2009/0105289 A1 Apr. 23, 2009

Related U.S. Application Data

(60) Provisional application No. 60/627,585, filed on Nov. 12, 2004.

(30) Foreign Application Priority Data

Oct. 12, 2004 (DK) .................................. 2004 01560

(51) Int. Cl.
*C07D 401/04* (2006.01)
*A61K 31/438* (2006.01)
(52) U.S. Cl. .......................................... 546/18; 514/278
(58) Field of Classification Search .................. 546/18; 514/278
See application file for complete search history.

(56) References Cited

U.S. PATENT DOCUMENTS

| | | |
|---|---|---|
| 2,913,454 A | 11/1959 | Petersen et al. |
| 3,723,442 A | 3/1973 | Nakanishi et al. |
| 3,784,551 A | 1/1974 | Nakanishi et al. |
| 4,350,696 A | 9/1982 | Cross et al. |
| 4,482,555 A | 11/1984 | Doria et al. |
| 4,851,423 A | 7/1989 | Girijavallabhan et al. |
| 4,963,590 A | 10/1990 | Backstrom et al. |
| 5,001,133 A | 3/1991 | Richardson et al. |
| 5,049,695 A | 9/1991 | Abraham et al. |
| 5,112,861 A | 5/1992 | Backstrom et al. |
| 5,122,539 A | 6/1992 | Abraham et al. |
| 5,169,850 A | 12/1992 | Dusza et al. |
| 5,225,402 A | 7/1993 | Ogawa et al. |
| 5,258,407 A | 11/1993 | Washburn et al. |
| 5,260,325 A | 11/1993 | Markwalder et al. |
| 5,272,167 A | 12/1993 | Girijavallabhan et al. |
| 5,274,104 A | 12/1993 | Arnaud et al. |
| 5,290,803 A | 3/1994 | Abraham et al. |
| 5,314,880 A | 5/1994 | Whittaker et al. |
| 5,356,904 A | 10/1994 | Freidinger et al. |
| 5,382,680 A | 1/1995 | Abraham et al. |
| 5,426,105 A | 6/1995 | Manning et al. |
| 5,432,191 A | 7/1995 | Abraham et al. |
| 5,436,254 A | 7/1995 | Ogawa et al. |
| 5,446,194 A | 8/1995 | Backstrom et al. |
| 5,459,144 A | 10/1995 | Girijavallabhan et al. |
| 5,585,394 A | 12/1996 | Di Malta et al. |
| 5,591,892 A | 1/1997 | Abraham et al. |
| 5,596,020 A | 1/1997 | Morris et al. |
| 5,602,137 A | 2/1997 | Ruhter et al. |
| 5,648,375 A | 7/1997 | Abraham et al. |
| 5,650,513 A | 7/1997 | Langhals et al. |
| 5,652,247 A | 7/1997 | Ogawa et al. |
| 5,674,879 A | 10/1997 | Manning et al. |
| 5,677,330 A | 10/1997 | Abraham et al. |
| 5,705,521 A | 1/1998 | Abraham et al. |
| 5,731,454 A | 3/1998 | Abraham et al. |
| 5,750,532 A | 5/1998 | Girijavallabhan et al. |
| 5,786,379 A | 7/1998 | Bernardon |
| 5,795,907 A | 8/1998 | Kalindjian et al. |
| 5,872,282 A | 2/1999 | Abraham et al. |

(Continued)

FOREIGN PATENT DOCUMENTS

| | | |
|---|---|---|
| CN | 1736485 | 2/2006 |
| DE | 4338784 | 5/1995 |
| FR | 2456731 | 12/1980 |
| GB | 825514 | 11/1956 |
| JP | 08-048662 | 2/1996 |

(Continued)

OTHER PUBLICATIONS

Orally Active, Nonpeptide Oxytocin Antagonist, Evans et al 1992.*
Search Report for PCT/EP2005/055181 dated Feb. 3, 2006.
XP-002363926, Chem Pharm Bull, 1993.
Evans, B. E. et al., Orally Active, Nonpeptide Oxytocin Antagonists, Journal Med. Chem., 1992, vol. 35, No. 21, pp. 3919-3927.
XP-002363927, Journal Chem. Soc., 1997.

(Continued)

*Primary Examiner* — Rita Desai
(74) *Attorney, Agent, or Firm* — Samuel B. Rollins

(57) ABSTRACT

A novel class of compounds of the general formula (I), their use in therapy, pharmaceutical compositions comprising the compounds, as well as their use in the manufacture of medicaments are described. The present compounds modulate the activity of 11 β-hydroxy-Steroid dehydrogenase type 1 (11βHSD1) and are accordingly useful in the treatment of diseases in which such a modulation is beneficial, e.g. the metabolic syndrome.

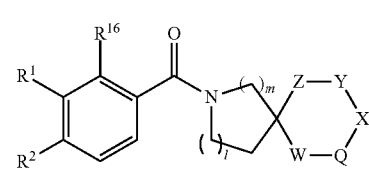

(I)

2 Claims, No Drawings

U.S. PATENT DOCUMENTS

| | | | |
|---|---|---|---|
| 5,912,260 A | 6/1999 | Kalindjian et al. | |
| 5,919,829 A | 7/1999 | Kalindjian et al. | |
| 5,927,283 A | 7/1999 | Abraham et al. | |
| 5,932,569 A | 8/1999 | Janssens et al. | |
| 5,939,437 A | 8/1999 | Kalindjian et al. | |
| 6,001,879 A | 12/1999 | Seitz et al. | |
| 6,096,736 A | 8/2000 | Ogawa et al. | |
| 6,124,289 A | 9/2000 | He et al. | |
| 6,458,803 B1 | 10/2002 | Sikorski et al. | |
| 6,506,783 B1 | 1/2003 | Camden | |
| 6,521,641 B1 | 2/2003 | Klein et al. | |
| 6,548,549 B1 | 4/2003 | Seitz et al. | |
| 6,613,803 B1 | 9/2003 | Wang et al. | |
| 6,638,947 B2 | 10/2003 | Wang et al. | |
| 6,696,442 B2 | 2/2004 | Wang et al. | |
| 6,833,371 B2 | 12/2004 | Atkinson et al. | |
| 7,129,242 B2 | 10/2006 | Satoh et al. | |
| 7,157,490 B2 | 1/2007 | Colandrea et al. | |
| 7,186,735 B2 | 3/2007 | Strobel et al. | |
| 7,265,122 B2 | 9/2007 | Wu et al. | |
| 7,358,238 B2 | 4/2008 | Andersen et al. | |
| 7,501,405 B2 | 3/2009 | Kampen et al. | |
| 7,557,110 B2 | 7/2009 | Kataoka et al. | |
| 7,700,583 B2 | 4/2010 | Gundertofte et al. | |
| 7,723,323 B2 | 5/2010 | Andersen et al. | |
| 2002/0006932 A1 | 1/2002 | Galley et al. | |
| 2002/0115671 A1 | 8/2002 | Goehring | |
| 2003/0144256 A1 | 7/2003 | Klein et al. | |
| 2004/0142922 A1 | 7/2004 | Alanine et al. | |
| 2004/0186102 A1 | 9/2004 | Wu et al. | |
| 2005/0009871 A1 | 1/2005 | Ramesh et al. | |
| 2005/0054850 A1 | 3/2005 | Wu et al. | |
| 2005/0080087 A1 | 4/2005 | Pendri et al. | |
| 2005/0154202 A1 | 7/2005 | Hagmann et al. | |
| 2005/0261302 A1 | 11/2005 | Hoff et al. | |
| 2006/0009918 A1 | 1/2006 | Mallik et al. | |
| 2006/0079506 A1 | 4/2006 | Linders et al. | |
| 2006/0094699 A1 | 5/2006 | Kampen et al. | |
| 2006/0111366 A1 | 5/2006 | Andersen et al. | |
| 2006/0149070 A1 | 7/2006 | Rohde et al. | |
| 2006/0281773 A1 | 12/2006 | Patel et al. | |
| 2007/0054882 A1 | 3/2007 | Klein et al. | |
| 2007/0270408 A1 | 11/2007 | Andersen et al. | |
| 2008/0108598 A1 | 5/2008 | Andersen et al. | |
| 2009/0118259 A1 | 5/2009 | Kilburn et al. | |
| 2009/0124598 A1 | 5/2009 | Andersen et al. | |
| 2009/0137574 A1 | 5/2009 | Kampen et al. | |
| 2009/0264412 A1 | 10/2009 | Kampen et al. | |
| 2009/0264414 A1 | 10/2009 | Andersen et al. | |
| 2009/0306048 A1 | 12/2009 | Kilburn et al. | |
| 2009/0325932 A1 | 12/2009 | Ebdrup et al. | |
| 2010/0056600 A1 | 3/2010 | Ebdrup et al. | |
| 2010/0076041 A1 | 3/2010 | Kilburn et al. | |
| 2010/0087543 A1 | 4/2010 | Ebdrup et al. | |
| 2010/0120743 A1 | 5/2010 | Gundertofte et al. | |
| 2010/0137377 A1 | 6/2010 | Petersen et al. | |
| 2010/0168083 A1 | 7/2010 | Ebdrup | |
| 2010/0197658 A1 | 8/2010 | Andersen et al. | |
| 2010/0292215 A1 | 11/2010 | Ebdrup et al. | |
| 2010/0331366 A1 | 12/2010 | Ebdrup | |
| 2011/0003852 A1 | 1/2011 | Ebdrup | |
| 2011/0003856 A1 | 1/2011 | Ebdrup | |
| 2011/0039853 A1 | 2/2011 | Ebdrup | |
| 2011/0224244 A1 | 9/2011 | Polisetti et al. | |

FOREIGN PATENT DOCUMENTS

| | | |
|---|---|---|
| JP | 09-221476 | 8/1997 |
| JP | 11-152269 | 6/1999 |
| JP | 2001 139574 | 5/2001 |
| JP | 2003-286171 | 10/2003 |
| JP | 2007-231005 | 9/2007 |
| WO | WO 94/01113 | 1/1994 |
| WO | WO 94/18193 | 8/1994 |
| WO | WO 97/07789 | 3/1997 |
| WO | WO 97/22588 | 6/1997 |
| WO | WO 97/24328 | 7/1997 |
| WO | WO 98/46559 | 10/1998 |
| WO | WO 99/30699 | 6/1999 |
| WO | WO 99/61013 | 12/1999 |
| WO | WO 00/12074 | 3/2000 |
| WO | WO 00/46197 | 8/2000 |
| WO | WO 00/47558 | 8/2000 |
| WO | WO 00/63165 | 10/2000 |
| WO | WO 00/73283 | 12/2000 |
| WO | WO 01/02385 | 1/2001 |
| WO | WO 01/22969 | 4/2001 |
| WO | WO 01/32621 | 5/2001 |
| WO | WO 01/44213 | 6/2001 |
| WO | WO 01/64676 | 9/2001 |
| WO | WO 01/90090 | 11/2001 |
| WO | WO 01/90091 | 11/2001 |
| WO | WO 01/90092 | 11/2001 |
| WO | WO 01/90093 | 11/2001 |
| WO | WO 01/90094 | 11/2001 |
| WO | WO 02/00626 | 1/2002 |
| WO | WO 02/02797 | 1/2002 |
| WO | WO 02/10191 | 2/2002 |
| WO | WO 02/072084 | 9/2002 |
| WO | WO 02/076435 | 10/2002 |
| WO | WO 02/089781 | 11/2002 |
| WO | WO 02/094799 | 11/2002 |
| WO | WO 02/100819 | 12/2002 |
| WO | WO 03/000649 | 1/2003 |
| WO | WO 03/028641 | 4/2003 |
| WO | WO 03/028730 | 4/2003 |
| WO | WO 03/029245 | 5/2003 |
| WO | WO 03/037274 | 5/2003 |
| WO | WO 03/037900 | 5/2003 |
| WO | WO 03/065983 | 8/2003 |
| WO | WO 03/070732 | 8/2003 |
| WO | WO 03/086410 | 10/2003 |
| WO | WO 2004/024896 | 3/2004 |
| WO | WO 2004/024897 | 3/2004 |
| WO | WO 2004/033427 | 4/2004 |
| WO | WO 2004/052461 | 6/2004 |
| WO | WO 2004/056744 | 7/2004 |
| WO | WO 2004/056745 | 7/2004 |
| WO | WO 2004/065351 | 8/2004 |
| WO | WO 2004/075823 | 9/2004 |
| WO | WO 2004/087159 | 10/2004 |
| WO | WO 2004/089380 | 10/2004 |
| WO | WO 2004/089415 | 10/2004 |
| WO | WO 2004/089416 | 10/2004 |
| WO | WO 2004/089470 | 10/2004 |
| WO | WO 2004/089471 | 10/2004 |
| WO | WO 2004/089896 | 10/2004 |
| WO | WO 2004/091610 | 10/2004 |
| WO | WO 2005/013950 | 2/2005 |
| WO | WO 2005/028438 | 3/2005 |
| WO | WO 2005/032484 | 4/2005 |
| WO | WO 2005/035534 | 4/2005 |
| WO | WO 2005/085202 | 9/2005 |
| WO | WO 2005/095397 | 10/2005 |
| WO | WO 2005/115975 | 12/2005 |
| WO | WO 2006/009835 | 1/2006 |
| WO | WO 2006/014012 | 2/2006 |
| WO | WO 2006/028958 | 3/2006 |
| WO | WO 2006/044645 | 4/2006 |
| WO | WO 2006/048330 | 5/2006 |
| WO | WO 2006/055752 | 5/2006 |
| WO | WO 2006/094633 | 9/2006 |
| WO | WO 2006/105127 | 10/2006 |
| WO | WO 2006/113261 | 10/2006 |
| WO | WO 2006/136402 | 12/2006 |
| WO | WO 2007/046001 | 4/2007 |
| WO | WO 2007/051810 | 5/2007 |
| WO | WO 2007/051811 | 5/2007 |
| WO | WO 2007/058960 | 5/2007 |
| WO | WO 2007/059905 | 5/2007 |
| WO | WO 2007/066784 | 6/2007 |
| WO | WO 2007/107550 | 9/2007 |
| WO | WO 2007/109160 | 9/2007 |
| WO | WO 2007/115935 | 10/2007 |
| WO | WO 2007/144394 | 12/2007 |
| WO | WO 2008/002244 | 1/2008 |
| WO | WO 2008/006702 | 1/2008 |

| WO | WO 2008/006703 | 1/2008 |
| --- | --- | --- |
| WO | WO 2008/101885 | 8/2008 |
| WO | WO 2008/101886 | 8/2008 |
| WO | WO 2008/101907 | 8/2008 |
| WO | WO 2008/101914 | 8/2008 |
| WO | WO 2008/110196 | 9/2008 |
| WO | WO 2008/119017 | 10/2008 |
| WO | WO 2008/127924 | 10/2008 |
| WO | WO 2008/134221 | 11/2008 |
| WO | WO 2009/126863 | 10/2009 |
| WO | WO 2010/057126 | 5/2010 |
| WO | WO 2010/059618 | 5/2010 |

OTHER PUBLICATIONS

Desai, M. C. et al., Polymer Bound EDC (P-EDC): A Convenient Reagent for Formation of an Amide Bond, Tetrahedron Letters, vol. 34, No. 48, pp. 7685-7688, 1993.

Nieczypor, P. et al., Synthesis of Nitrogen-Containing Spiro Compounds from Lactams by Allylboration and Subsequent Ring-Closing Metathesis, Eur. J. Org. Chem., 2004, pp. 812-819.

Yang, L. et al., Potent 3-Spiropiperidine Growth Hormone Secretagogues, Bioorganic & Medicinal Chemistry Letters 8, 1998, pp. 107-112.

Johnson, R. A. et al, Stereochemistry of the Microbiological Oxygenation of N-Acylcyclohexylamines, Journal of Organic Chemistry, 1970, vol. 35, No. 3, pp. 622-626.

XP-002363928, J. Chem. Soc., 1990.

Tannin, G. M. et al., The Human Gene for 11β-Hydroxysteroid Dehydrogenase, Journal of Biological Chemistry, 1991, vol. 266, No. 25, pp. 16653-16658.

Bujalska, I. J. et al., Differentiation of Adipose Stromal Cells: The Roles of Glucocorticoids and 11β-Hydroxysteroid Dehydrogenase, Endocrinology, 1999, vol. 140, No. 7, pp. 3188-3196.

Whorwood, C. B. et al., Regulation of Glucocorticoid Receptor α and β Isoforms and Type I 11β-Hydroxysteroid Dehydrogenase Expression in Human Skeletal Muscle Cells: A Key Role in the Pathogenesis of Insulin Resistance?, Journal of Clinical Endocrinology & Metabolism, 2001, vol. 86, No. 5, pp. 2296-2308.

Cooper, M. S. et al.., Expression and Functional Consequences of 11β-Hydroxysteroid Dehydrogenase Activity in Human Bone, Bone, 2000, vol. 27, No. 3, pp. 375-381.

Davani, B. et al, Type 1 11β-Hydroxysteroid Dehydrogenase Mediates Glucocorticoid Activation and Insulin Release in Pancreatic Islets, Journal of Biological Chemistry,2000, vol. 275, No. 45, pp. 34841-34844.

Brem, A. S. et al, Localization of 2 11β=OH Steroid Dehydrogenase Isoforms in Aortic Endothelial Cells, Hypertension, 1998, vol. 31, No. 2, pp. 459-462.

Rauz, S. et al., Expression and Putative Role of 11β-Hydroxysteroid Dehydrogenase Isozymes within the Human Eye, Investigative Ophthalmology & Visual Science, Aug. 2001, vol. 42, No. 9, p. 2037-2042.

Moisan, M-P. et al., 11β-Hydroxysteroid Dehydrogenase Bioactivity and Messenger RNA Expression in Rat Forebrain: Localization in Hypothalamus, Hippocampus, and Cortex, Endocrinology, 1990, vol. 127, No. 3, pp. 1450-1455.

Andrews, R. C. et al., Effects of the 11β-Hydroxysteroid Dehydrogenase Inhibitor Carbenoxolone on Insulin Sensitivity in Men with Type 2 Diabetes, Journal of Clinical Endocrinology & Metabolism, 2003, vol. 88, No. 1, pp. 285-291.

Walker B. R. et al. Carbenoxolone Increases Hepatic Insulin Sensitivity in Man: A Novel Role for 11-Oxosteroid Reductase in Enhancing Glucocorticoid Receptor Activation, Journal of Clinical Endocrinology and Metabolism, 1995, vol. 80, No. 11, pp. 3155-3159.

Morton, N.M. et al. Improved Lipid and Lipoprotein Profile, Hepatic Insulin Sensitivity, and Glucose Tolerance in 11βHydroxysteroid Dehydrogenase Type 1 Null Mice, The Journal of Biological Chemistry, 2001, vol. 276, No. 44, pp. 41293-41300.

Koteletsev, Y. et al., 11β-Hydroxysteroid dehydrogenase type 1 knockout mice show attenuated glucocorticoid-inducible responses and resist hyperglycemia on obesity or stress, Proc. Natl. Acad. Sci. USA, Dec. 1997 vol. 94, pp. 14924-14929.

Masuzaki, H. et al., A Transgenic Model of Visceral Obesity and the Metabolic Syndrome, Dec. 7, 2001, vol. 294, pp. 2166-2170.

Souness, G. W. et al, 11β-Hydroxysteroid dehydrogenase antisense affects vascular contractile response and glucocorticoid metabolism, Steroids, 2002, vol. 67, pp. 195-201.

Brindely, D. N. et al., Hormonal Regulation of the Hepatic Low Density Lipoprotein Receptor and the Catabolism of Low Density Lipoproteins: Relationship with the Secretion of Very Low Density Lipoproteins, Prog. Lipid Res., vol. 30, No. 4, pp. 349-360, 1991.

Andrew et al., J. Clin. Endocrinol. Metab. vol. 87, pp. 277-285 (2002).

Barf T et al: "Recent progress in 11-[beta]-hydroxysteroid dehydrogenase type 1 (11-[beta]-HSD1) inhibitor development" Drugs of the Future 2006 Spain, vol. 31, No. 3, Mar. 2006, pp. 231-243.

Bird et al., J. Physiology vol. 585, pp. 187-201 (2007).

Carruthers et al., J. Chem. Soc. Perkin Trans. 1 vol. 10, pp. 2854-2856 (1990).

Coppola, Gary M. et al., "Perhydroquinolylbenzamides as Novel Inhibitors of 11.beta.-Hydroxysteroid Dehydrogenase Type 1" Journal of Medicinal Chemistry, 48 (21), 6696-6712 Coden: Jmcmar; ISSN: 0022-2623, 2005.

Demchenko, Chem. Hetero. Comp. vol. 36, pp. 985-988 (2000).

Donohue et al., J. Comb. Chem. vol. 4, pp. 23-32 (2002).

Fotsch C. et al., "11[beta]-Hydroxysteroid dehydrogenase-1 as a therapeutic target for metabolic diseases" Expert Opinion on Therapeutic Patents, Ashley Publications, GB, vol. 15, No. 3, 2005, pp. 289-303.

Ganguly A.K. et al.; "Sythesis of heterocyclic compounds using radical reactions" Tetrahedron Letters, Elsevier, Amsterdam, NL, vol. 43, No. 38, Sep. 16, 2002, pp. 6865-6868.

Giacomelli et al. Eur. J. Org. Chem. vol. 3, pp. 537-541 (2003).

Hashigaki et al., Chem. Pharm. Bull. vol. 32, pp. 3561-3568 (1984).

Hosfield et al., J. Biol. Chem. vol. 280, pp. 4639-4648 (2005).

Ignatova et al., American Journal of Physiology—Endocrinology and Metabolism, 296(2):E367-E377 (2009).

Kondo, Kazumi et al: "Characterization of Orally Active Nonpeptide Vasopressin V2 Receptor Agonist" Journal of Medicinal Chemistry, vol. 45, No. 17, 2002, pp. 3805-3808.

Kondo, Kazumi et al: "Novel Design of Nonpeptide AVP V2 Receptor Agonists: Structural Requirements for and Agonist Having 1-(4-Aminobenzoyl)-2,3,4,5,-tetrahydro-1H-1-benezazepine as a Template" Journal of Medicinal Chemistry, vol. 43, No. 23, 2000, pp. 4388-4397.

Leyendecker et al., Nouveau J. de Chimie vol. 9, pp. 13-19 (1985).

Mariani et al., Farmaco vol. 38, pp. 653-663 (1983).

Massa et al., J. Heterocycl. Chem. vol. 27, pp. 1805-1808 (1990).

Masuzaki et al., J. Clin. Invest. vol. 112, pp. 83-90 (2003).

McCullough et al., J. Chem. Soc. Perkin Trans. 1 vol. 20, pp. 2553-2560 (1996).

Nankervis et al.: "Calcium sensitizazion as a positive inotropic mechanism . . . " Journal of Cardiovascular Pharmacology, vol. 24, No. 4, 1994, pp. 612-617.

PCT International Preliminary Report on Patentability for Application No. PCT/EP2005/055181 dated Apr. 17, 2007.

Pending Claims for U.S. Appl. No. 12/092,223, filed Mar. 24, 2011.
Pending Claims for U.S. Appl. No. 12/092,230, filed Mar. 25, 2011.
Pending Claims for U.S. Appl. No. 12/293,709, filed Mar. 25, 2011.
Pending Claims for U.S. Appl. No. 12/294,475, filed Jul. 18, 2011.
Pending Claims for U.S. Appl. No. 12/304,501, filed Mar. 25, 2011.
Pending Claims for U.S. Appl. No. 12/307,999, filed May 23, 2011.
Pending Claims for U.S. Appl. No. 12/308,000, filed Mar. 28, 2011.
Pending Claims for U.S. Appl. No. 12/528,227, filed Mar. 28, 2011.
Pending Claims for U.S. Appl. No. 12/528,229, filed Mar. 29, 2011.
Pending Claims for U.S. Appl. No. 12/528,231, filed Mar. 28, 2011.
Pending Claims for U.S. Appl. No. 12/528,233, filed Mar. 29, 2011.
Pending Claims for U.S. Appl. No. 12/529,956, filed Mar. 29, 2011.
Pending Claims for U.S. Appl. No. 12/593,456, filed Mar. 29, 2011.
Pending Claims for U.S. Appl. No. 12/595,310, filed Mar. 29, 2011.
Pending Claims for U.S. Appl. No. 12/597,129, filed Mar. 29, 2011.
Pending Claims for U.S. Appl. No. 13/078,221, filed Apr. 1, 2011.
Pending Claims for U.S. Appl. No. 13/220,843, filed Aug. 30, 2011.
Reed et al., Scand. J. Gastroentreol. vol. 15, pp. 51-56 (1980).

Schwartz et al., Nature vol. 404, pp. 661-671 (2000).

Seefelter et al., Chemische Berichte vol. 96, pp. 3243-3253 (1963).

Skowronska-Ptasinska et al: "Effect of Different Dialkylamino Groups on the Regioselectivity of Lithiation of 0-Protected 3-(Dialkylamino)phenols" Journal of Organic Chemistry, vol. 50, No. 15, 1985, pp. 2690-2698.

Sohar R et al: "Conformational Analysis of N-Acylazabycyclooctanes," Magnetic Resonance in Chemistry, John Wiley, Chichester, GB, vol. 23, No. 7, Jan. 1, 1985, pp. 506-513.

Tabuchi, S. et al.: "Novel Potent Antagonists of Human Neuropeptide Y Y5 Receptor. Part 1: 2-Oxobenzothiazolin-3-acetic Acid Derivatives" Bioorganic & Medicinal Chemistry Letters, vol. 12, 2002, pp. 1171-1175.

Tomlinson et al., J. Clin. Endocrinol. Metab. vol. 87, pp. 57-62 (2002).

Villani, F.J. et al.; "Derivatives of 2-Azabicyclo[2.2.2]octane" Journal of Medicinal Chemistry, 1966, pp. 264-265.

Whitworth et al., J. Hypertens. vol. 20, pp. 1035-1043 (2002).

Willoughby C A et al: "Solid Phase Synthesis of Aryl Amines" Tetrahedron Letters, Elsevier, Amsterdam, NL, vol. 37, No. 40, Sep. 30, 1996, pp. 7181-7184 XP004030858 ISSN: 0040-4039 table 2; compound 1.

Wu et al., Toxicology vol. 236, pp. 1-6 (2007).

Yau et al., Proc. Nat'l Acad. Sci. vol. 98, pp. 4716-4721 (2001).

Yudt et al., Mol. Endocrinol. vol. 16, pp. 1719-1726 (2002).

* cited by examiner

11β-HYDROXYSTEROID DEHYDROGENASE TYPE 1 ACTIVE SPIRO COMPOUNDS

CROSS-REFERENCE TO RELATED APPLICATIONS

This application is a 35 U.S.C. §371 National Stage Application of International Patent Application PCT/EP2005/055181 (published as WO 2006/040329), filed Oct. 12, 2005, which claimed priority of Danish Patent Application PA 2004 01560, filed Oct. 12, 2004; this application further claims priority under 35 U.S.C. §119 of U.S. Provisional Application 60/627,585, filed Nov.12, 2004.

FIELD OF INVENTION

The present invention relates to novel spirocyclic amides, to their use in therapy, to pharmaceutical compositions comprising the compounds, to the use of said compounds in the manufacture of medicaments, and to therapeutic methods comprising the administration of said compounds. The present compounds modulate the activity of 11β-hydroxysteroid dehydrogenase type 1 (11βHSD1) and are accordingly useful in the treatment of diseases in which such a modulation is beneficial, such as the metabolic syndrome.

BACKGROUND OF THE INVENTION

The metabolic syndrome is a major global health problem. In the US, the prevalence in the adult population is currently estimated to be approximately 25%, and it continues to increase both in the US and worldwide. The metabolic syndrome is characterized by a combination of insulin resistance, dyslipidemia, obesity and hypertension leading to increased morbidity and mortality of cardiovascular diseases. People with the metabolic syndrome are at increased risk of developing frank type 2 diabetes, the prevalence of which is equally escalating.

In type 2 diabetes, obesity and dyslipidemia are also highly prevalent and around 70% of people with type 2 diabetes additionally have hypertension once again leading to increased mortality of cardiovascular diseases.

In the clinical setting, it has long been known that glucocorticoids are able to induce all of the cardinal features of the metabolic syndrome and type 2 diabetes.

11β-hydroxysteroid dehydrogenase type 1 (11βHSD1) catalyses the local generation of active glucocorticoid in several tissues and organs including predominantly the liver and adipose tissue, but also e.g. skeletal muscle, bone, pancreas, endothelium, ocular tissue and certain parts of the central nervous system. Thus, 11βHSD1 serves as a local regulator of glucocorticoid actions in the tissues and organs where it is expressed (Tannin et al., *J. Biol. Chem.*, 266,16653 (1991); Bujalska et al., *Endocrinology*, 140, 3188 (1999); Whorwood et al., *J. Clin. Endocrinol. Metab.*, 86, 2296 (2001); Cooper et al., *Bone*, 27, 375 (2000); Davani et al., *J. Biol. Chem.*, 275, 34841 (2000); Brem et al., *Hypertension*, 31, 459 (1998); Rauz et al., *Invest. Opthalmol. Vis. Sci.*, 42, 2037 (2001); Moisan et al., *Endocrinology*, 127, 1450 (1990)).

The role of 11βHSD1 in the metabolic syndrome and type 2 diabetes is supported by several lines of evidence. In humans, treatment with the non-specific 11βHSD1 inhibitor carbenoxolone improves insulin sensitivity in lean healthy volunteers and people with type 2 diabetes. Likewise, 11βHSD1 knock-out mice are resistant to insulin resistance induced by obesity and stress. Additionally, the knock-out mice present with an anti-atherogenic lipid profile of decreased VLDL triglycerides and increased HDL-cholesterol. Conversely, mice that overexpress 11βHSD1 in adipocytes develop insulin resistance, hyperlipidemia and visceral obesity, a phenotype that resembles the human metabolic syndrome (Andrews et al., *J. Clin. Endocrinol. Metab.*, 88, 285 (2003); Walker et al., *J. Clin. Endocrinol. Metab.*, 80, 3155 (1995); Morton et al., *J. Biol. Chem.* 276, 41293 (2001); Kotelevtsev et al., *Proc. Natl. Acad. Sci. USA*, 94,14924 (1997); Masuzaki et al., Science, 294, 2166 (2001)).

The more mechanistic aspects of 11βHSD1 modulation and thereby modulation of intracellular levels of active glucocorticoid have been investigated in several rodent models and different cellular systems. 11βHSD1 promotes the features of the metabolic syndrome by increasing hepatic expression of the rate-limiting enzymes in gluconeogenesis, namely phosphoenolpyuvate carboxykinase and glucose-6-phosphatase, promoting the differentiation of preadipocytes into adipocytes thus facilitating obesity, directly and indirectly stimulating hepatic VLDL secretion, decreasing hepatic LDL uptake and increasing vessel contractility (Kotelevtsev et al., *Proc. Natl. Acad. Sci. USA*, 94, 14924 (1997); Morton et al., *J. Biol. Chem.* 276, 41293 (2001); Bujalska et al., *Endocrinology*, 140, 3188 (1999); Souness et al., *Steroids*, 67,195 (2002); Brindley & Salter, *Prog. Lipid Res.*, 30, 349 (1991)).

WO 01/90090, WO 01/90091, WO 01/90092, WO 01/90093 and WO 01/90094 discloses various thiazol-sulfonamides as inhibitors of the human 11β-hydroxysteroid dehydrogenase type 1 enzyme, and further states that said compounds may be useful in treating diabetes, obesity, glaucoma, osteoporosis, cognitive disorders, immune disorders and depression.

We have now found novel spirocyclic amides that modulate the activity of 11βHSD1 leading to altered intracellular concentrations of active glucocorticoid. More specifically, the present compounds inhibit the activity of 11βHSD1 leading to decreased intracellular concentrations of active glucocorticoid. Thus, the present compounds can be used to treat disorders where a decreased level of active intracellular glucocorticoid is desirable, such as e.g. the metabolic syndrome, type 2 diabetes, impaired glucose tolerance (IGT), impaired fasting glucose (IFG), dyslipidemia, obesity, hypertension, diabetic late complications, cardiovascular diseases, arteriosclerosis, atherosclerosis, myopathy, muscle wasting, osteoporosis, neurodegenerative and psychiatric disorders, and adverse effects of treatment or therapy with glucocorticoid receptor agonists.

Objects of the present invention are to provide compounds, pharmaceutical compositions and use of said compounds that modulate the activity of 11βHSD1.

DEFINITIONS

In the following structural formulas and throughout the present specification, the following terms have the indicated meaning:

The term "halo" includes fluorine, chlorine, bromine, and iodine.

The term "trihalomethyl" includes trifluoromethyl, trichloromethyl, tribromomethyl, and triiodomethyl.

The term "trihalomethoxy" includes trifluorometoxy, trichlorometoxy, tribromometoxy, and triiodometoxy.

The term "alkyl" includes $C_1$-$C_8$, e.g. $C_1$-$C_6$ or $C_1$-$C_3$ straight chain saturated and methylene aliphatic hydrocarbon groups, $C_3$-$C_8$ branched saturated hydrocarbon groups having the specified number of carbon atoms. For example, this definition shall include but is not limited to methyl (Me), ethyl (Et), propyl (Pr), butyl (Bu), pentyl, hexyl, isopropyl (i-Pr), isobutyl (i-Bu), tert-butyl (t-Bu), sec-butyl (s-Bu), isopentyl, neopentyl, and the like.

The term "alkenyl" includes $C_2$-$C_6$ straight chain unsaturated aliphatic hydrocarbon groups and branched $C_3$-$C_6$ unsaturated aliphatic hydrocarbon groups having the specified number of carbon atoms. For example, this definition shall include but is not limited to ethenyl, propenyl, butenyl, pentenyl, hexenyl, methylpropenyl, methylbutenyl and the like.

The term "alkynyl" includes $C_2$-$C_6$ straight chain unsaturated aliphatic hydrocarbon groups and $C_4$-$C_6$ branched unsaturated aliphatic hydrocarbon groups having the specified number of carbon atoms. For example, this definition shall include but is not limited to ethynyl, propynyl, butynyl, pentynyl, hexynyl, methylbutynyl, and the like.

The term "saturated or partially saturated cyclic, bicyclic or tricyclic ring system" represents but are not limited to azepanyl, azocanyl, 1,2,3,4-tetrahydro-quinolinyl, 1,2,3,4-tetrahydro-isoquinolinyl, 1,2,3,4-tetrahydro-quinoxalinyl, indolinyl, 6-aza-bicyclo[3.2.1]octane, 2-aza-bicyclo[4.1.1]octane, 2-aza-bicyclo[3.2.1]octanyl, 7-aza-bicyclo[4.1.1]octanyl, 9-aza-bicyclo[3.3.2]decanyl, 4-aza-tricyclo[4.3.1.1$^{3,8}$] undecanyl, 9-aza-tricyclo[3.3.2.0$^{3.7}$]decanyl, 8-aza-spiro [4.5]decane.

The term "cycloalkyl" (e.g. cyclopropyl, cyclobutyl, cyclopentyl, cyclohexyl, cycloheptyl, cyclooctyl, cyclononyl, cyclodecyl, bicyclo[3.2.1]octyl, spiro[4.5]decyl, norpinyl, norbonyl, norcaryl, adamantyl and the like) represents a saturated, mono-, bi-, tri- or spirocarbocyclic group having the specified number of carbon atoms.

The term "cycloalkylalkyl" (e.g. cyclopropylmethyl, cyclobutylethyl, adamantylmethyl and the like) represents a cycloalkyl group as defined above attached through an alkyl group having the indicated number of carbon atoms or substituted alkyl group as defined above.

The term "cycloalkenyl" (e.g. cyclobutenyl, cyclopentenyl, cyclohexenyl, cycloheptenyl, cyclooctenyl, cyclononenyl, cyclodecenyl and the like) represents a partially saturated, mono-, bi-, tri- or spirocarbocyclic group having the specified number of carbon atoms.

The term "cycloalkylcarbonyl" (e.g. cyclopropylcarbonyl, cyclohexylcarbonyl) represents a cycloalkyl group as defined above having the indicated number of carbon atoms attached through a carbonyl group.

The term "cycloalkylalkylcarbonyl" (e.g. 1-cyclohexyl-propylcarbonyl, ethyl-cyclopentyl-ethylcarbonyl, 4-cycloheptyl-3-methyl-butyl-2-carbonyl) represents an cycloalkyl group as defined above having the indicated number of carbon atoms attached through an alkyl group having the indicated number of carbon atoms or substituted alkyl group as defined above and attached through an carbonyl group.

The term "cycloalkyloxy" (e.g. cyclohexyloxy, cycloheptyloxy, cyclopentyloxy) represents an cycloalkyl group as defined above having the indicated number of carbon atoms attached through an oxygen bridge.

The term "cycloalkyloxycarbonyl" (e.g. cyclohexyloxycarbonyl, cycloheptyloxycarbonyl, cyclopentyloxycarbonyl) represents a cycloalkyloxy group as defined above having the indicated number of carbon atoms attached through an carbonyl group.

The term "hetcycloalkylcarbonyl" (e.g. 1-piperidin-4-yl-carbonyl, 1-(1,2,3,4-tetrahydro-isoquinolin-6-yl)carbonyl) represents an hetcycloalkyl group as defined above having the indicated number of carbon atoms attached through a carbonyl group.

The term "hetcycloalkyl" (e.g. tetrahydrofuranyl, tetrahydropyranyl, tertahydrothiopyranyl, piperidine, pyridazine and the like) represents a saturated mono-, bi-, tri- or spiro-carbocyclic group having the specified number of carbon atoms and one or two additional heteroatoms or groups selected from nitrogen, oxygen, sulphur, SO or $SO_2$.

The term "hetcycloalkylalkyl" (e.g. tetrahydrofuranylmethyl, tetrahydropyranylethyl, tertahydrothiopyranylmethyl, and the like) represents a hetcycloalkyl group as defined above attached through an alkyl group having the indicated number of carbon atoms or substituted alkyl group as defined above.

The term "hetcycloalkyloxy" (e.g. tetrahydro-furanyloxy, piperidyloxy, azepanyloxy) represents an hetcycloalkyl group as defined above having the indicated number of carbon atoms attached through an oxygen bridge.

The term "alkyloxy" (e.g. methoxy, ethoxy, propyloxy, allyloxy, cyclohexyloxy) represents an alkyl group as defined above having the indicated number of carbon atoms attached through an oxygen bridge.

The term "alkyloxyalkyl" (e.g. methyloxymethyl, ethyloxymethyl, ethyloxyethyl, isopropyloxymethyl, tert-butyloxyethyl and the like) represents an alkyloxy group as defined above attached through an "alkyl" group.

The term "aryloxy" (e.g. phenoxy, naphthyloxy and the like) represents an aryl group as defined below attached through an oxygen bridge.

The term "hetaryloxy" (e.g. 2-pyridyloxy, 2-pyrimidyloxy, 2-imidazolyloxy and the like) represents a hetaryl group as defined below attached through an oxygen bridge.

The term "aryloxyalkyl" (e.g. phenoxymethyl, naphthyloxyethyl and the like) represents an aryloxy group as defined above attached through an "alkyl" group having the indicated number of carbon atoms.

The term "arylalkyloxy" (e.g. phenethyloxy, naphthylmethyloxy and the like) represents an arylalkyl group as defined below attached through an oxygen bridge.

The term "hetarylalkyloxy" (e.g. 2-pyridylmethyloxy and the like) represents a hetarylalkyl group as defined below attached through an oxygen bridge.

The term "hetaryloxyalkyl" (e.g. 2-pyridyloxymethyl, 2-quinolyloxyethyl and the like) represents a hetaryloxy group as defined above attached through an "alkyl" group having the indicated number of carbon atoms.

The term "hetarylalkyloxyalkyl" (e.g. 4-methoxymethylpyrimidine, 2-methoxymethylquinoline and the like) represents a hetarylalkyloxy group as defined above attached through an "alkyl" group having the indicated number of carbon atoms.

The term "arylalkyloxyalkyl" (e.g. ethoxymethyl-benzene, 2-methoxymethylnaphthalene and the like) represents an arylalkyloxy group as defined above attached through an "alkyl" group having the indicated number of carbon atoms.

The term "alkylthio" (e.g. methylthio, ethylthio and the like) represents an alkyl group as defined above attached through a sulphur bridge.

The term "alkyloxycarbonyl" (e.g. methylformiat, ethylformiat and the like) represents an alkyloxy group as defined above attached through a carbonyl group.

The term "aryloxycarbonyl" (e.g. phenylformiat, 2-thiazolylformiat and the like) represents an aryloxy group as defined above attached through a carbonyl group.

The term "arylalkyloxycarbonyl" (e.g. benzylformiat, phenyletylformiat and the like) represents an "arylalkyloxy" group as defined above attached through a carbonyl group.

The term "arylalkyl" (e.g. benzyl, phenylethyl, 3-phenylpropyl, 1-naphtylmethyl, 2-(1-naphtyl)ethyl and the like) represents an aryl group as defined below attached through an alkyl having the indicated number of carbon atoms or substituted alkyl group as defined above.

The term "hetarylalkyl" (e.g. (2-furyl)methyl, (3-furyl)methyl, (2-thienyl)methyl, (3-thienyl)methyl, (2-pyridyl)methyl, 1-methyl-1-(2-pyrimidyl)ethyl and the like) represents a hetaryl group as defined below attached through an alkyl having the indicated number of carbon atoms or substituted alkyl group as defined above.

The term "alkylcarbonyl" (e.g. octylcarbonyl, pentylcarbonyl, 3-hexenylcarbonyl) represents an alkyl group as defined above having the indicated number of carbon atoms attached through a carbonyl group.

The term "arylcarbonyl" (e.g. benzoyl) represents an aryl group as defined below attached through a carbonyl group.

The term "hetarylcarbonyl" (e.g. 2-thiophenylcarbonyl, 3-methoxy-anthrylcarbonyl, oxazolylcarbonyl and the like) represents a hetaryl group as defined below attached through a carbonyl group.

The term "alkylcarbonylalkyl" (e.g. propan-2-one, 4,4-dimethyl-pentan-2-one and the like) represents an alkylcarbonyl group as defined above attached through an alkyl group as defined above having the indicated number of carbon atoms.

The term "hetarylcarbonylalkyl" (e.g. 1-pyridin-2-yl-propan-1-one, 1-(1-H-imidazol-2-yl)-propan-1-one and the like) represents a hetarylcarbonyl group as defined above attached through an alkyl group as defined above having the indicated number of carbon atoms.

The term "arylalkylcarbonyl" (e.g. phenylpropylcarbonyl, phenylethylcarbonyl and the like) represents an arylalkyl group as defined above having the indicated number of carbon atoms attached through a carbonyl group.

The term "hetarylalkylcarbonyl" (e.g. imidazolylpentylcarbonyl and the like) represents a hetarylalkyl group as defined above wherein the alkyl group is in turn attached through a carbonyl.

The term "alkylcarboxy" (e.g. heptylcarboxy, cyclopropylcarboxy, 3-pentenylcarboxy) represents an alkylcarbonyl group as defined above wherein the carbonyl is in turn attached through an oxygen bridge.

The term "arylcarboxy" (e.g. benzoic acid and the like) represents an arylcarbonyl group as defined above wherein the carbonyl is in turn attached through an oxygen bridge.

The term "alkylcarboxyalkyl" (e.g. heptylcarboxymethyl, propylcarboxy tert-butyl, 3-pentylcarboxyethyl) represents an alkylcarboxy group as defined above wherein the carboxy group is in turn attached through an alkyl group as defined above having the indicated number of carbon atoms.

The term "arylalkylcarboxy" (e.g. benzylcarboxy, phenylpropylcarboxy and the like) represents an arylalkylcarbonyl group as defined above wherein the carbonyl is in turn attached through an oxygen bridge.

The term "hetarylalkylcarboxy" (e.g. (1-H-imidazol-2-yl)-acetic acid, 3-pyrimidin-2-yl-propionic acid and the like) represents a hetarylalkylcarbonyl group as defined above wherein the carbonyl is in turn attached through an oxygen bridge.

The term "alkylS(O)$_n$" (e.g. ethylsulfonyl, ethylsulfinyl and the like) represents an alkyl group as defined above, wherein the alkyl group is in turn attached through a sulphur bridge wherein the sulphur is substituted with n oxygen atoms.

The term "arylS(O)$_n$" (e.g. phenylsulfinyl, naphthyl-2-sulfonyl and the like) represents an aryl group as defined above, wherein the aryl group is in turn attached through a sulphur bridge wherein the sulphur is substituted with n oxygen atoms.

The term "hetarylS(O)$_n$" (e.g. 2-sulfonyl-pyridyl, 4-sulfinyl-1H-imidazolyl, 6-sulfonylindolyl and the like) represents an hetaryl group as defined above, wherein the hetaryl group is in turn attached through a sulphur bridge wherein the sulphur is substituted with n oxygen atoms.

The term "arylalkylS(O)$_n$" (e.g. benzylsulfinyl, phenetyl-2-sulfonyl and the like) represents an arylalkyl group as defined above, wherein the arylalkyl group is in turn attached through a sulphur bridge wherein the sulphur is substituted with n oxygen atoms.

The term "aryl" includes but is not limited to a carbocyclic aromatic ring system being either monocyclic, bicyclic, or polycyclic, such as phenyl, biphenyl, naphthyl, anthracenyl, phenanthrenyl, fluorenyl, indenyl, pentalenyl, azulenyl, biphenylenyl and the like. Aryl is also intended to include the partially hydrogenated derivatives of the carbocyclic aromatic systems enumerated above. Non-limiting examples of such partially hydrogenated derivatives are 1,2,3,4-tetrahydronaphthyl, 1,4-dihydronaphthyl and the like.

The term "hetaryl" includes but is not limited to pyrrolyl (2-pyrrolyl), pyrazolyl (3-pyrazolyl), imidazolyl (1-imidazolyl, 2-imidazolyl, 4-imidazolyl, 5-imidazolyl), triazolyl (1,2,3-triazol-1-yl, 1,2,3-triazol-2-yl 1,2,3-triazol-4-yl, 1,2,4-triazol-3-yl), oxazolyl (2-oxazolyl, 4-oxazolyl, 5-oxazolyl), isoxazolyl (3-isoxazolyl, 4-isoxazolyl, 5-isoxazolyl), thiazolyl (2-thiazolyl, 4-thiazolyl, 5-thiazolyl), thiophenyl (2-thiophenyl, 3-thiophenyl, 4-thiophenyl, 5-thiophenyl), furanyl (2-furanyl, 3-furanyl, 4-furanyl, 5-furanyl), pyridyl (2-pyridyl, 3-pyridyl, 4-pyridyl, 5-pyridyl), 5-tetrazolyl, pyrimidinyl (2-pyrimidinyl, 4-pyrimidinyl, 5-pyrimidinyl, 6-pyrimidinyl), pyrazinyl, pyridazinyl (3-pyridazinyl, 4-pyridazinyl, 5-pyridazinyl), quinolyl (2-quinolyl, 3-quinolyl, 4-quinolyl, 5-quinolyl, 6-quinolyl, 7-quinolyl, 8-quinolyl), isoquinolyl (1-isoquinolyl, 3-isoquinolyl, 4-isoquinolyl, 5-isoquinolyl, 6-isoquinolyl, 7-isoquinolyl, 8-isoquinolyl), benzo[b]furanyl (2-benzo[b]furanyl, 3-benzo[b]furanyl, 4-benzo[b]furanyl, 5-benzo[b]furanyl, 6-benzo[b]furanyl, 7-benzo[b]furanyl), 2,3-dihydro-benzo[b]furanyl (2-(2,3-dihydro-benzo[b]-furanyl), 3-(2,3-dihydro-benzo[b]furanyl), 4-(2,3-dihydro-benzo[b]furanyl), 5-(2,3-dihydro-benzo[b]furanyl), 6-(2,3-dihydro-benzo[b]furanyl), 7-(2,3-dihydro-benzo[b]furanyl)), benzo[b]thiophenyl (2-benzo[b]thiophenyl, 3-benzo[b]thiophenyl, 4-benzo[b]thiophenyl, 5-benzo[b]thiophenyl, 6-benzo[b]thiophenyl, 7-benzo[b]thiophenyl), 2,3-dihydro-benzo[b]thiophenyl (2-(2,3-dihydro-benzo[b]thiophenyl), 3-(2,3-dihydro-benzo[b]thiophenyl), 4-(2,3-dihydro-benzo[b]thiophenyl), 5-(2,3-dihydro-benzo[b]thiophenyl), 6-(2,3-dihydro-benzo[b]thiophenyl), 7-(2,3-dihydro-benzo[b]thiophenyl)), 4,5,6,7-tetrahydro-benzo[b]thiophenyl (2-(4,5,6,7-tetrahydro-benzo[b]thiophenyl), 3-(4,5,6,7-tetrahydro-benzo[b]thiophenyl), 4-(4,5,6,7-tetrahydro-benzo[b]thiophenyl), 5-(4,5,6,7-tetrahydro-benzo[b]thiophenyl), 6-(4,5,6,7-tetrahydro-benzo[b]thiophenyl), 7-(4,5,6,7-tetrahydro-benzo[b]thiophenyl)), thieno[2,3-b]thiophenyl, 4,5,6,7-tetrahydro-thieno [2,3-c]pyridyl (4-(4,5,6,7-tetrahydro-thieno[2,3-c]pyridyl), 5-4,5,6,7-tetrahydro-thieno[2,3-c]pyridyl), 6-(4,5,6,7-tetrahydro-thieno[2,3-c]pyridyl), 7-(4,5,6,7-tetrahydro-thieno[2,3-c]pyridyl)), indolyl (1-indolyl, 2-indolyl, 3-indolyl, 4-indolyl, 5-indolyl, 6-indolyl, 7-indolyl), isoindolyl (1-isoindolyl, 2-isoindolyl, 3-isoindolyl, 4-isoindolyl, 5-isoindolyl, 6-isoindolyl, 7-isoindolyl), 1,3-dihydro-isoindolyl (1-(1,3-dihydro-isoindolyl), 2-(1,3-dihydro-isoindolyl), 3-(1,3-dihydro-isoindolyl), 4-(1,3-dihydro-isoindolyl), 5-(1,3-dihydro-isoindolyl), 6-(1,3-dihydro-isoindolyl), 7-(1,3-dihydro-isoindolyl)), indazole (1-indazolyl, 3-indazolyl, 4-indazolyl, 5-indazolyl, 6-indazolyl, 7-indazolyl), benzimidazolyl (1-benzimidazolyl, 2-benzimidazolyl, 4-benzimidazolyl, 5-benzimidazolyl, 6-benzimidazolyl, 7-benzimidazolyl, 8-benzimidazolyl), benzoxazolyl (1-benz-oxazolyl, 2-benzoxazolyl), benzothiazolyl (1-benzothiazolyl, 2-benzothiazolyl, 4-benzothiazolyl, 5-benzothiazolyl, 6-benzothiazolyl, 7-benzothiazolyl), benzo-[1,2,5]oxadiazolyl, (4-benzo[1,2,5]oxadiazole, 5-benzo[1,2,5]oxadiazole), carbazolyl (1-carbazolyl, 2-carbazolyl, 3-carbazolyl, 4-carbazolyl), piperidinyl (2-piperidinyl, 3-piperidinyl, 4-piperidinyl), pyrrolidinyl (1-pyrrolidinyl, 2-pyrrolidinyl, 3-pyrrolidinyl).

The term "$R^9$alkylcarbonyl" or "$R^{11}$alkylcarbonyl" (e.g. 2-cyclohexyloxy-acetyl, 3-(1-methyl-piperidin-4-yloxy)-propionyl, 2-phenoxy-acetyl and the like) represents an $R^9$ or an $R^{11}$ group as defined above attached through an alkylcarbonyl group as defined above.

The term "$R^{11}$carbonyl" (e.g. acetyl, 3-phenyl-propionyl, phenyl-acetyl, 2-(pyridin-2-ylmethoxy)-acetyl and the like) represents an $R^{11}$ group as defined above attached through a carbonyl group.

The term "$R^{11}$carbonylN($R^7$)" (e.g. 3-phenyl-propionamide, phenyl-acetamide, 2-(pyridin-2-ylmethoxy)-acetamide, N-methyl-2-(pyridin-2-ylmethoxy)-acetamide, benzyl-2-(pyridin-3-ylmethoxy)-acetamide and the like) represents an $R^{11}$carbonyl group as defined above attached through an amino group substituted with $R^7$ as defined above.

The term "$NR^7R^8$-carbonylalkyl" (e.g. N,N-dimethyl-propionamide, N-isopropyl-N-methyl-propionamide and the like) represents an $NR^7R^8$ group attached through a carbonylalkyl group as defined above.

The term "$NR^7R^8$alkylcarbonyl" (e.g. N,N-dimethylamino-acetyl, (N-cyclohexyl-N-methyl-amino)-acetyl, 2-(4-acetyl-piperazin-1-yl)-acetyl and the like) represents an $NR^7R^8$ group attached through an alkylcarbonyl group as defined above.

The term "$NR^7R^8oxoC_1$-$C_6$alkyl" (e.g. 1-ethoxy-piperidine, N-benzyl-N-methyl-O-propyl-hydroxylamine, 1-isopropoxy-azepane, 1-ethoxy-4-phenyl-piperazine, 1-(1-ethoxypiperidin-4-yl)-ethanone and the like) represents an $NR^7R^8$ group attached through an oxygen bridge attached through an alkyl group as defined above.

Certain of the above defined terms may occur more than once in the structural formulae, and upon such occurrence each term shall be defined independently of the other.

The term "optionally substituted" as used herein means that the groups in question are either unsubstituted or substituted with one or more of the substituents specified. When the groups in question are substituted with more than one substituent the substituents may be the same or different.

The term "treatment" is defined as the management and care of a patient for the purpose of combating or alleviating the disease, condition or disorder, and the term includes the administration of the active compound to prevent the onset of the symptoms or complications, or alleviating the symptoms or complications, or eliminating the disease, condition, or disorder.

The term "pharmaceutically acceptable" is defined as being suitable for administration to humans without adverse events.

The term "prodrug" is defined as a chemically modified form of the active drug, said prodrug being administered to the patient and subsequently being converted to the active drug. Techniques for development of prodrugs are well known in the art.

DETAILED DESCRIPTION OF THE INVENTION

The present invention is based on the observation that the compounds of the general formula (I) disclosed below are able to modulate or inhibit the activity of 11βHSD1.

Accordingly, the present invention is concerned with compounds or prodrugs thereof of the general formula (I)

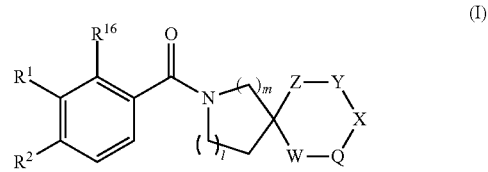

(I)

wherein
m and l are each independently 0, 1, 2, 3, 4, or 5, with the proviso that m+l is equal to 1, 2, 3, 4 or 5;
$R^1$ and $R^2$ independently are hydrogen, $C_1$-$C_6$alkyl, —$NR^3R^4$ or —$OR^5$, wherein the alkyl group is optionally substituted with one or more of $R^6$; or
$R^1$ and $R^2$ together with the carbon atoms to which they are attached, are forming a saturated or partially saturated 5- to 7-membered cyclic ring system containing 0 to 3 heteroatoms selected from nitrogen, oxygen or sulphur, the ring system optionally being substituted with one or more of $R^6$;
$R^{16}$ is hydrogen or —$OR^5$; or
when $R^{16}$ is —$OR^5$, $R^1$ and $R^5$ together with the carbon and oxygen atoms to which they are attached, may form a saturated or unsaturated benzo[b]furanyl ring system, the ring system optionally being substituted with one or more of $R^6$;
W, Q and X independently are an optional covalent bond, —$(CR^{17}R^{18})_p$—, —$N(R^6)$—, —O—, —S— or $S(O)_n$—;
Y and Z independently are an optional covalent bond, —$(CR^{17}R^{18})$—, —$N(R^6)$—, —O—, —S— or —$S(O)_n$—; or
Y and Z considered together are 2 adjoining atoms forming a $C_3$-$C_{10}$cycloalkyl or $C_3$-$C_{10}$-hetcycloalkyl, aryl or hetaryl, wherein the cycloalkyl, hetcycloalkyl, aryl and hetaryl groups independently are optionally substituted with one or more of $R^6$; or
Q, X and Y considered together are 2 adjoining atoms forming a $C_3$-$C_{10}$cycloalkyl or $C_3$-$C_{10}$-hetcycloalkyl, aryl or hetaryl, wherein the cycloalkyl, hetcycloalkyl, aryl and hetaryl groups independently are optionally substituted with one or more of $R^6$;
$R^3$ is hydrogen, $C_1$-$C_6$alkyl, $C_3$-$C_{10}$cycloalkyl, $C_3$-$C_{10}$cycloalkyl$C_1$-$C_6$alkyl, $C_1$-$C_6$alkyloxy$C_1$-$C_6$-alkyl, aryl$C_1$-$C_6$alkyloxy$C_1$-$C_6$alkyl or $C_2$-$C_6$alkenyl;
$R^4$ is $C_1$-$C_6$alkyl, $C_3$-$C_{10}$cycloalkyl, $C_3$-$C_{10}$cycloalkyl$C_1$-$C_6$alkyl, aryl$C_1$-$C_6$alkyl, hetaryl$C_1$-$C_6$-alkyl; $C_3$-$C_{10}$cycloalkylcarbonyl-, $C_3$-$C_{10}$hetcycloalkylcarbonyl-, $C_3$-$C_{10}$hetcycloalkyl$C_1$-$C_6$-alkylcarbonyl-, arylcarbonyl-, hetarylcarbonyl-, $C_1$-$C_6$alkyloxy$C_1$-$C_6$alkyl, aryloxy$C_1$-$C_6$alkyl, aryl$C_1$-$C_6$alkyloxy$C_1$-$C_6$alkyl, hetaryl$C_1$-$C_6$alkyloxy$C_1$-$C_6$alkyl, $NR^7R^8$-carbonyl$C_1$-$C_6$alkyl-, $R^9C_1$-$C_6$alkylcarbonyl-, $C_1$-$C_6$alkylS(O)$_n$—, arylS(O)$_n$—, aryl$C_1$-$C_6$alkyl-S(O)$_n$—, or $NR^7R^8oxoC_1$-$C_6$-alkyl, wherein the aryl and hetaryl groups independently are optionally substituted with one or more $R^6$; or
$R^3$ and $R^4$ together with the nitrogen to which they are attached, are forming a saturated or partially saturated cyclic, bicyclic or tricyclic ring system containing from 4 to 12 carbon atoms and from 0 to 2 additional heteroatoms selected from nitrogen or oxygen, the ring system optionally being substituted with at least one or more $R^{13}$;

$R^5$ is $C_1$-$C_6$alkyl, $C_3$-$C_{10}$cycloalkyl, $C_3$-$C_{10}$cycloalkyl$C_1$-$C_6$alkyl, aryl, hetaryl, aryl$C_1$-$C_6$alkyl, hetaryl$C_1$-$C_6$alkyl, $C_1$-$C_6$alkyloxo$C_1$-$C_6$alkyl, aryl$C_1$-$C_6$alkyloxo$C_1$-$C_6$alkyl, $NR^7R^8$oxo$C_1$-$C_6$alkyl or $NR^7R^8$-carbonyl$C_1$-$C_6$alkyl, wherein the alkyl and aryl groups independently are optionally substituted with one or more $R^6$;

$R^6$ is hydrogen, halo, hydroxy, oxo, cyano, $C_1$-$C_8$alkyl, $C_3$-$C_{10}$cycloalkyl, trihalomethyl, trihalomethyloxy, aryl, aryl$C_1$-$C_6$alkyl, —$COR^{10}$, $C_1$-$C_6$alkylcarbonyl-, $C_3$-$C_{10}$cycloalkylcarbonyl-, $C_3$-$C_{10}$cycloalkyl$C_1$-$C_6$alkylcarbonyl-, arylcarbonyl-, aryl$C_1$-$C_6$alkylcarbonyl-, hetarylcarbonyl-, hetaryl$C_1$-$C_6$alkylcarbonyl-, $C_1$-$C_6$alkyloxy-, aryloxy-, aryl$C_1$-$C_6$alkyloxy-, hetaryloxy-, hetaryl-$C_1$-$C_6$alkyloxy-, $C_1$-$C_6$alkyloxy$C_1$-$C_6$alkyl, aryloxy$C_1$-$C_6$alkyl, aryl$C_1$-$C_6$alkyloxy$C_1$-$C_6$alkyl, hetaryl, hetaryl$C_1$-$C_6$alkyl, hetaryloxy$C_1$-$C_6$alkyl, hetaryl$C_1$-$C_6$alkyloxy$C_1$-$C_6$alkyl, —$NR^7R^8$, —$SO_2NR^7R^8$, $NR^7R^8$-carbonyl$C_1$-$C_6$alkyl, $R^{11}$carbonylN($R^7$)—, $C_1$-$C_6$alkylS(O)$_n$—, arylS(O)$_n$—, hetarylS(O)$_n$— or $R^{12}$S(O)$_n$N($R^7$)—; wherein the aryl and hetaryl groups independently are optionally substituted with one or more $R^{13}$;

$R^7$ and $R^8$ independently are hydrogen, $C_1$-$C_8$alkyl, $C_3$-$C_{10}$cycloalkyl, $C_3$-$C_{10}$cycloalkyl$C_1$-$C_6$-alkyl, $C_3$-$C_{10}$hetcycloalkyl, aryl, hetaryl, aryl$C_1$-$C_6$alkyl or hetaryl$C_1$-$C_6$alkyl wherein the alkyl, aryl and hetaryl groups independently are optionally substituted with one or more of $R^{13}$; or $R^7$ and $R^8$ together with the nitrogen to which they are attached, are forming a saturated or partially saturated cyclic, bicyclic or tricyclic ring system containing from 4 to 12 carbon atoms and from 0 to 2 additional heteroatoms selected from nitrogen or oxygen, the ring system optionally being substituted with at least one or more $R^{13}$;

$R^3$ is $C_1$-$C_6$alkyl, $C_3$-$C_{10}$cycloalkyl, $C_3$-$C_{10}$cycloalkyl$C_1$-$C_6$alkyl, $C_3$-$C_{10}$hetcycloalkyl-, $C_3$-$C_{10}$-cycloalkylcarbonyl-, $C_3$-$C_{10}$hetcycloalkylcarbonyl-, arylcarbonyl-, hetarylcarbonyl-, $C_1$-$C_6$-alkyloxy, aryloxy, aryl$C_1$-$C_6$alkyloxy, $C_3$-$C_{10}$cycloalkyloxy, $C_3$-$C_{10}$hetcycloalkyloxy-, $C_1$-$C_6$-alkyloxy$C_1$-$C_6$alkyl, $NR^7R^8$-carbonyl$C_1$-$C_6$alkyl-, $R^{11}C_1$-$C_6$alkylcarbonyl-, $C_1$-$C_6$alkylS(O)$_n$—, arylS(O)$_p$—, aryl$C_1$-$C_6$alkylS(O)$_n$—, aryl$C_1$-$C_6$alkyl or hetaryl$C_1$-$C_6$alkyl, wherein the aryl and hetaryl groups independently are optionally substituted with one or more $R^{11}$;

$R^{10}$ is hydroxy, $C_1$-$C_8$alkyloxy, —$NR^7R^8$, aryloxy or aryl$C_1$-$C_6$alkyloxy;

$R^{11}$ is $C_1$-$C_6$alkyl, $C_2$-$C_6$alkenyl, aryl, aryl$C_1$-$C_6$alkyl, hetaryl, hetaryl$C_1$-$C_6$alkyl, $C_3$-$C_{10}$cycloalkyl, $C_3$-$C_{10}$hetcycloalkyl, $C_1$-$C_6$alkyloxy-, aryloxy-, aryl$C_1$-$C_6$alkyloxy-, hetaryloxy-, hetaryl$C_1$-$C_6$alkyloxy-, $C_1$-$C_6$alkyloxycarbonyl-, aryloxycarbonyl-, aryl$C_1$-$C_6$alkyloxycarbonyl-, $C_3$-$C_{10}$-cycloalkyloxycarbonyl, aryl$C_1$-$C_6$alkyloxy$C_1$-$C_6$alkyl-, hetaryl$C_1$-$C_6$alkyloxy$C_1$-$C_6$alkyl- or $R^7R^8NC_1$-$C_6$alkyl- wherein the alkyl, alkenyl, cycloalkyl, hetcycloalkyl, aryl and hetaryl groups are optionally substituted with $R^{14}$;

$R^{12}$ is $C_1$-$C_6$alkyl, $C_3$-$C_{10}$cycloalkyl, $C_3$-$C_{10}$hetcycloalkyl, aryl, aryl$C_1$-$C_6$alkyl, hetaryl, hetaryl$C_1$-$C_6$alkyl;

$R^{13}$ is $R^3$, —$NR^7R^8$, oxo, $C_1$-$C_6$alkyl, $C_3$-$C_{10}$cycloalkyl or $C_3$-$C_{10}$hetcycloalkyl, aryl, hetaryl, wherein the alkyl, cycloalkyl, hetcycloalkyl, aryl and hetaryl groups independently are optionally substituted with one or more of $R^{15}$;

$R^{14}$ is hydrogen, halo, hydroxy, oxo, nitro, cyano or —$COR^{10}$, $C_1$-$C_8$alkyl, —$NR^7R^8$, $C_1$-$C_6$-alkyloxy or aryl$C_1$-$C_6$alkyl;

$R^{15}$ is $C_1$-$C_8$alkyl, $C_1$-$C_6$alkyloxy or aryl$C_1$-$C_6$alkyl;

$R^{17}$ and $R^{18}$ independently are hydrogen, hydroxy, cyano, $C_1$-$C_8$alkyl, trihalomethyl, trihalomethyloxy, aryl, aryl$C_1$-$C_6$alkyl, —$COR^{10}$, $C_1$-$C_6$alkyloxy-, aryloxy-, aryl$C_1$-$C_6$alkyloxy-, hetaryloxy-, hetaryl$C_1$-$C_6$alkyloxy-, $C_1$-$C_6$alkyloxy$C_1$-$C_6$alkyl, aryloxy$C_1$-$C_6$alkyl, aryl$C_1$-$C_6$alkyloxy$C_1$-$C_6$alkyl, hetaryl, hetaryl$C_1$-$C_6$alkyl, hetaryloxy$C_1$-$C_6$alkyl, hetaryl$C_1$-$C_6$alkyloxy$C_1$-$C_6$alkyl, —$NR^7R^8$, —$SO_2NR^7R^8$, $NR^7R^8$carbonyl$C_1$-$C_6$alkyl, $R^{11}$carbonylN($R^7$)—, arylS(O)$_n$—, hetarylS(O)$_n$— or $R^{12}$S(O)$_n$N($R^7$)—; wherein the aryl and hetaryl groups independently are optionally substituted with one or more $R^{13}$; or $R^{17}$ and $R^{18}$ together with the carbon atom to which they are attached are —C(=O)—;

n is 1 or 2;

p is 1 or 2; or a salt thereof with a pharmaceutically acceptable acid or base, or any optical isomer or mixture of optical isomers, including a racemic mixture, or any tautomeric forms.

In one embodiment of the present invention, in formula (I), m and l are each independently 0, 1, 2 or 3.

In another embodiment of the present invention, in formula (I), m and l are each independently 0, 1 or 2.

In another embodiment of the present invention, in formula (I), m is 1 and l is 0.

In another embodiment of the present invention, in formula (I), m is 1 and l is 1.

In another embodiment of the present invention, in formula (I), m is 2 and l is 1.

In another embodiment of the present invention, in formula (I), m is 1 and l is 3.

In another embodiment of the present invention, in formula (I), m+l is equal to 2 or 3.

In another embodiment of the present invention, in formula (I), one of $R^1$ and $R^2$ is hydrogen and the other is $C_1$-$C_6$alkyl, —$NR^3R^4$ or —$OR^5$, wherein $R^3$, $R^4$ and $R^5$ are as defined above.

In another embodiment of the present invention, in formula (I), one of $R^1$ and $R^2$ is hydrogen and the other is $C_1$-$C_6$alkyl.

In another embodiment of the present invention, in formula (I), one of $R^1$ and $R^2$ is hydrogen and the other is —$NR^3R^4$, wherein $R^3$ and $R^4$ are as defined above.

In another embodiment of the present invention, in formula (I), one of $R^1$ and $R^2$ is hydrogen and the other is —$OR^5$, wherein $R^5$ is as defined above.

In another embodiment of the present invention, in formula (I), one of $R^1$ and $R^2$ is $C_1$-$C_6$alkyl and the other is —$NR^3R^4$, wherein $R^3$ and $R^4$ are as defined above.

In another embodiment of the present invention, in formula (I), one of $R^1$ and $R^2$ is $C_1$-$C_6$alkyl and the other is —$OR^5$, wherein $R^5$ is as defined above.

In another embodiment of the present invention, in formula (I), one of $R^1$ and $R^2$ is —$NR^3R^4$ and the other is —$OR^5$, wherein $R^3$, $R^4$ and $R^5$ are as defined above.

In another embodiment of the present invention, in formula (I), $R^{16}$ is hydrogen.

In another embodiment of the present invention, in formula (I), $R^{16}$ is —$OR^5$, wherein $R^5$ is as defined above.

In another embodiment of the present invention, in formula (I), $R^1$ and $R^5$ together with the carbon and oxygen atoms to which they are attached, are forming a saturated or unsaturated benzo[b]furanyl ring system.

In another embodiment of the present invention, in formula (I), $R^1$ and $R^2$ together with the carbon atoms to which they are attached, are forming a saturated or partially saturated 5-membered cyclic ring system containing no heteroatoms, the ring system optionally being substituted with one or more of $R^6$, wherein $R^6$ is as defined above.

In another embodiment of the present invention, in formula (I), $R^1$ and $R^2$ together with the carbon atoms to which they are attached, are forming a saturated or partially saturated 5-membered cyclic ring system containing 1 heteroatom selected from nitrogen, oxygen or sulphur, the ring system optionally being substituted with one or more of $R^6$, wherein $R^6$ is as defined above.

In another embodiment of the present invention, in formula (I), $R^1$ and $R^2$ together with the carbon atoms to which they are attached, are forming a saturated or partially saturated 5-membered cyclic ring system containing 2 heteroatoms selected from nitrogen, oxygen or sulphur, the ring system optionally being substituted with one or more of $R^6$, wherein $R^6$ is as defined above.

In another embodiment of the present invention, in formula (I), $R^1$ and $R^2$ together with the carbon atoms to which they are attached, are forming a saturated or partially saturated 5-membered cyclic ring system containing 3 heteroatoms selected from nitrogen, oxygen or sulphur, the ring system optionally being substituted with one or more of $R^6$, wherein $R^6$ is as defined above.

In another embodiment of the present invention, in formula (I), $R^1$ and $R^2$ together with the carbon atoms to which they are attached, are forming a saturated or partially saturated 5-membered cyclic ring system containing 1 or 2 nitrogen atoms, the ring system optionally being substituted with one or more of $R^6$, wherein $R^6$ is as defined above.

In another embodiment of the present invention, in formula (I), $R^1$ and $R^2$ together with the carbon atoms to which they are attached, are pyrrolyl, imidazolyl, pyrazolyl, triazolyl, furanyl, dihydro-furanyl, oxazolyl, thiazolyl, isoxazolyl, thiophenyl.

In another embodiment of the present invention, in formula (I), $R^1$ and $R^2$ together with the carbon atoms to which they are attached, are forming a saturated or partially saturated 6-membered cyclic ring system containing no heteroatoms, the ring system optionally being substituted with one or more of $R^6$, wherein $R^6$ is as defined above.

In another embodiment of the present invention, in formula (I), $R^1$ and $R^2$ together with the carbon atoms to which they are attached, are forming a saturated or partially saturated 6-membered cyclic ring system containing 1 heteroatom selected from nitrogen, oxygen or sulphur, the ring system optionally being substituted with one or more of $R^6$, wherein $R^6$ is as defined above.

In another embodiment of the present invention, in formula (I), $R^1$ and $R^2$ together with the carbon atoms to which they are attached, are forming a saturated or partially saturated 6-membered cyclic ring system containing 2 heteroatoms selected from nitrogen, oxygen or sulphur, the ring system optionally being substituted with one or more of $R^6$, wherein $R^6$ is as defined above.

In another embodiment of the present invention, in formula (I), $R^1$ and $R^2$ together with the carbon atoms to which they are attached, are forming a saturated or partially saturated 6-membered cyclic ring system containing 3 heteroatoms selected from nitrogen, oxygen or sulphur, the ring system optionally being substituted with one or more of $R^6$, wherein $R^6$ is as defined above.

In another embodiment of the present invention, in formula (I), $R^1$ and $R^2$ together with the carbon atoms to which they are attached, are cyclohexanyl, piperidyl, tetrahydropyranyl, morpholinyl, pyridyl, pyridazinyl, pyrimidyl, pyrazinyl.

In another embodiment of the present invention, in formula (I), $R^1$ and $R^2$ together with the carbon atoms to which they are attached, are forming a saturated or partially saturated 7-membered cyclic ring system containing no heteroatoms, the ring system optionally being substituted with one or more of $R^6$, wherein $R^6$ is as defined above.

In another embodiment of the present invention, in formula (I), $R^1$ and $R^2$ together with the carbon atoms to which they are attached, are forming a saturated or partially saturated 7-membered cyclic ring system containing 1 heteroatom selected from nitrogen, oxygen or sulphur, the ring system optionally being substituted with one or more of $R^6$, wherein $R^6$ is as defined above.

In another embodiment of the present invention, in formula (I), $R^1$ and $R^2$ together with the carbon atoms to which they are attached, are forming a saturated or partially saturated 7-membered cyclic ring system containing 2 heteroatoms selected from nitrogen, oxygen or sulphur, the ring system optionally being substituted with one or more of $R^6$, wherein $R^6$ is as defined above.

In another embodiment of the present invention, in formula (I), $R^1$ and $R^2$ together with the carbon atoms to which they are attached, are forming a saturated or partially saturated 7-membered cyclic ring system containing 3 heteroatoms selected from nitrogen, oxygen or sulphur, the ring system optionally being substituted with one or more of $R^6$, wherein $R^6$ is as defined above.

In another embodiment of the present invention, in formula (I), $R^1$ and $R^2$ together with the carbon atoms to which they are attached, is azepanyl.

In another embodiment of the present invention, in formula (I), W, Q and X independently are an optional covalent bond, $—(CR^{17}R^{18})_p—$ or $—N(R^6)—$, wherein $R^{17}$, $R^{18}$, $R^6$ and p are as defined above.

In another embodiment of the present invention, in formula (I), W is a covalent bond.

In another embodiment of the present invention, in formula (I), W is $—(CR^{17}R^{18})_p—$, wherein $R^{17}$, $R^{18}$ and p are as defined above.

In another embodiment of the present invention, in formula (I), W is $—(CR^{17}R^{18})—$, wherein $R^{17}$ and $R^{18}$ are as defined above.

In another embodiment of the present invention, in formula (I), W is $—N(R^6)—$, wherein $R^6$ is as defined above.

In another embodiment of the present invention, in formula (I), W is $—O—$, $—S—$ or $—S(O)_n—$, wherein n is as defined above.

In another embodiment of the present invention, in formula (I), Q is a covalent bond.

In another embodiment of the present invention, in formula (I), Q is $—(CR^{17}R^{18})_p—$, wherein $R^{17}$, $R^{18}$ and p are as defined above.

In another embodiment of the present invention, in formula (I), Q is $—(CR^{17}R^{18})—$, wherein $R^{17}$ and $R^{15}$ are as defined above.

In another embodiment of the present invention, in formula (I), Q is $—N(R^6)—$, wherein $R^6$ is as defined above.

In another embodiment of the present invention, in formula (I), Q is $—O—$, $—S—$ or $—S(O)_n—$, wherein n is as defined above.

In another embodiment of the present invention, in formula (I), X is a covalent bond.

In another embodiment of the present invention, in formula (I), X is $—(CR^{17}R^{18})_p—$, wherein $R^{17}$, $R^{18}$ and p are as defined above.

In another embodiment of the present invention, in formula (I), X is —$(CR^{17}R^{18})$—, wherein $R^{17}$ and $R^{18}$ are as defined above.

In another embodiment of the present invention, in formula (I), X is —$N(R^6)$—, wherein $R^6$ is as defined above.

In another embodiment of the present invention, in formula (I), X is —O—, —S— or —$S(O)_n$—, wherein n is as defined above.

In another embodiment of the present invention, in formula (I), Y and Z independently are an optional covalent bond, —$(CR^{17}R^{18})_p$— or —$N(R^6)$—, wherein $R^{17}$, $R^{18}$, $R^6$ and p are as defined above.

In another embodiment of the present invention, in formula (I), Y is a covalent bond.

In another embodiment of the present invention, in formula (I), Y is —$(CR^{17}R^{18})_p$—, wherein $R^{17}$, $R^{18}$ and p are as defined above.

In another embodiment of the present invention, in formula (I), Y is —$(CR^{17}R^{18})$—, wherein $R^{17}$ and $R^{18}$ are as defined above.

In another embodiment of the present invention, in formula (I), Y is —$N(R^6)$—, wherein $R^6$ is as defined above.

In another embodiment of the present invention, in formula (I), Y is —O—, —S— or —$S(O)_n$—, wherein n is as defined above.

In another embodiment of the present invention, in formula (I), Z is a covalent bond.

In another embodiment of the present invention, in formula (I), Z is —$(CR^{17}R^{18})_p$—, wherein $R^{17}$, $R^{13}$ and p are as defined above.

In another embodiment of the present invention, in formula (I), Z is —$(CR^{17}R^{18})$—, wherein $R^{17}$ and $R^{18}$ are as defined above.

In another embodiment of the present invention, in formula (I), Z is —$N(R^6)$—, wherein $R^6$ is as defined above.

In another embodiment of the present invention, in formula (I), Z is —O—, —S— or —$S(O)_n$—, wherein n is as defined above.

In another embodiment of the present invention, in formula (I), Y and Z together are 2 adjoining atoms forming a $C_3$-$C_{10}$cycloalkyl optionally substituted with one or more of $R^6$, wherein $R^6$ is as defined above.

In another embodiment of the present invention, in formula (I), Y and Z together are 2 adjoining atoms forming a $C_3$-$C_{10}$hetcycloalkyl optionally substituted with one or more of $R^6$, wherein $R^6$ is as defined above.

In another embodiment of the present invention, in formula (I), Y and Z together are 2 adjoining atoms forming an aryl optionally substituted with one or more of $R^6$, wherein $R^6$ is as defined above.

In another embodiment of the present invention, in formula (I), Y and Z together are 2 adjoining atoms forming a hetaryl optionally substituted with one or more of $R^6$, wherein $R^6$ is as defined above.

In another embodiment of the present invention, in formula (I), Q, X and Y together are 2 adjoining atoms forming a $C_3$-$C_{10}$cycloalkyl optionally substituted with one or more of $R^6$, wherein $R^6$ is as defined above.

In another embodiment of the present invention, in formula (I), Q, X and Y together are 2 adjoining atoms forming a $C_3$-$C_{10}$hetcycloalkyl optionally substituted with one or more of $R^6$, wherein $R^6$ is as defined above.

In another embodiment of the present invention, in formula (I), Q, X and Y together are 2 adjoining atoms forming an aryl optionally substituted with one or more of $R^6$, wherein $R^6$ is as defined above.

In another embodiment of the present invention, in formula (I), Q, X and Y together are 2 adjoining atoms forming a hetaryl optionally substituted with one or more of $R^6$, wherein $R^6$ is as defined above.

In another embodiment of the present invention, in formula (I), $R^3$ is hydrogen, $C_1$-$C_6$alkyl, $C_3$-$C_{10}$cycloalkyl, $C_3$-$C_{10}$cycloalkyl$C_1$-$C_6$alkyl, $C_1$-$C_6$alkyloxy$C_1$-$C_6$alkyl.

In another embodiment of the present invention, in formula (I), $R^3$ is hydrogen, $C_1$-$C_6$alkyl, $C_3$-$C_{10}$cycloalkyl, $C_3$-$C_{10}$cycloalkyl$C_1$-$C_6$alkyl.

In another embodiment of the present invention, in formula (I), $R^3$ is hydrogen or $C_1$-$C_6$alkyl.

In another embodiment of the present invention, in formula (I), $R^4$ is $C_1$-$C_6$alkyl, $C_3$-$C_{10}$cycloalkyl, $C_3$-$C_{10}$cycloalkyl$C_1$-$C_6$alkyl, aryl$C_1$-$C_6$alkyl, hetaryl$C_1$-$C_6$alkyl.

In another embodiment of the present invention, in formula (I), $R^4$ is $C_1$-$C_6$alkyl.

In another embodiment of the present invention, in formula (I), $R^4$ is $C_1$-$C_6$alkyloxy-$C_1$-$C_6$alkyl, aryloxy$C_1$-$C_6$alkyl, aryl$C_1$-$C_6$alkyloxy$C_1$-$C_6$alkyl, hetaryl$C_1$-$C_6$alkyloxy$C_1$-$C_6$alkyl, $NR^7R^8$carbonyl$C_1$-$C_6$alkyl-, $R^9C_1$-$C_6$alkylcarbonyl- or $NR^7R^8$oxo$C_1$-$C_6$alkyl, wherein the aryl and hetaryl groups independently are optionally substituted with one or more $R^6$, wherein $R^7$, $R^8$, $R^9$ and $R^6$ are as defined above.

In another embodiment of the present invention, in formula (I), $R^4$ is $C_1$-$C_6$alkyloxy-$C_1$-$C_6$alkyl, aryloxy$C_1$-$C_6$alkyl, aryl$C_1$-$C_6$alkyloxy$C_1$-$C_6$alkyl, hetaryl$C_1$-$C_6$alkyloxy$C_1$-$C_6$alkyl, $NR^7R^8$carbonyl$C_1$-$C_6$alkyl- or $R^9C_1$-$C_6$alkylcarbonyl-, wherein the aryl and hetaryl groups independently are optionally substituted with one or more $R^6$, wherein $R^7$, $R^8$, $R^9$ and $R^8$ are as defined above.

In another embodiment of the present invention, in formula (I), $R^4$ is aryloxy$C_1$-$C_6$-alkyl, aryl$C_1$-$C_6$alkyloxy$C_1$-$C_6$alkyl, hetaryl$C_1$-$C_6$alkyloxy$C_1$-$C_6$alkyl, $NR^7R^8$carbonyl$C_1$-$C_6$alkyl- or $R^9C_1$-$C_6$alkylcarbonyl-, wherein the aryl and hetaryl groups independently are optionally substituted with one or more $R^6$, wherein $R^7$, $R^8$, $R^9$ and $R^6$ are as defined above.

In another embodiment of the present invention, in formula (I), $R^3$ and $R^4$ together with the nitrogen to which they are attached, are forming a saturated or partially saturated cyclic or bicyclic ring system containing from 4 to 12 carbon atoms and from 0 to 2 additional heteroatoms selected from nitrogen or oxygen, the ring system optionally being substituted with at least one or more $R^{13}$, wherein $R^{13}$ is as defined above.

In another embodiment of the present invention, in formula (I), $R^3$ and $R^4$ together with the nitrogen to which they are attached, are forming a saturated or partially saturated cyclic or bicyclic ring system containing from 6 to 10 carbon atoms and from 0 to 2 additional heteroatoms selected from nitrogen or oxygen, the ring system optionally being substituted with at least one or more $R^{13}$, wherein $R^{13}$ is as defined above.

In another embodiment of the present invention, in formula (I), $R^3$ and $R^4$ together with the nitrogen to which they are attached, are forming a saturated or partially saturated cyclic or bicyclic ring system containing from 6 to 10 carbon atoms and from 1 to 2 additional heteroatoms selected from nitrogen or oxygen, the ring system optionally being substituted with at least one or more $R^{13}$, wherein $R^{13}$ is as defined above.

In another embodiment of the present invention, in formula (I), $R^5$ is $C_3$-$C_{10}$Cycloalkyl, $C_3$-$C_{10}$cycloalkyl$C_1$-$C_6$alkyl, aryl$C_1$-$C_6$alkyl, hetaryl$C_1$-$C_6$alkyl, $C_1$-$C_6$alkyloxo$C_1$-$C_6$alkyl, aryl$C_1$-$C_6$alkyloxo$C_1$-$C_6$alkyl, $NR^7R^8$oxo$C_1$-$C_6$alkyl or $NR^7R^8$carbonyl$C_1$-$C_6$alkyl, wherein the alkyl and aryl groups independently are optionally substituted with one or more $R^6$, wherein $R^7$, $R^8$ and $R^6$ are as defined above.

In another embodiment of the present invention, in formula (I), $R^5$ is $C_3$-$C_{10}$cycloalkyl, $C_3$-$C_{10}$cycloalkyl$C_1$-$C_6$alkyl, aryl$C_1$-$C_6$alkyl, hetaryl$C_1$-$C_6$alkyl, aryl$C_1$-$C_6$alkyloxo$C_1$-$C_6$-alkyl, $NR^7R^8$oxo$C_1$-$C_6$alkyl or $NR^7R^8$carbonyl$C_1$-$C_6$alkyl, wherein the alkyl and aryl groups independently are optionally substituted with one or more $R^6$, wherein $R^7$, $R^8$ and $R^6$ are as defined above.

In another embodiment of the present invention, in formula (I), $R^5$ is $C_3$-$C_{10}$cycloalkyl$C_1$-$C_6$alkyl, aryl$C_1$-$C_6$alkyl, hetaryl$C_1$-$C_6$alkyl, $C_1$-$C_6$alkyloxo$C_1$-$C_6$alkyl, aryl$C_1$-$C_6$alkyloxo$C_1$-$C_6$alkyl or $NR^7R^8$carbonyl$C_1$-$C_6$alkyl, wherein the alkyl and aryl groups independently are optionally substituted with one or more $R^6$, wherein $R^7$, $R^8$ and $R^6$ are as defined above.

In another embodiment of the present invention, in formula (I), $R^6$ is hydrogen, halo, hydroxy, oxo, $C_1$-$C_8$alkyl, $C_3$-$C_{10}$cycloalkyl, trihalomethyl, trihalomethyloxy, aryl, aryl$C_1$-$C_6$alkyl, $C_1$-$C_6$alkylcarbonyl-, $C_3$-$C_{1-10}$cyclo-alkyl-carbonyl-, $C_3$-$C_{10}$cycloalkyl$C_1$-$C_6$alkylcarbonyl-, arylcarbonyl-, aryl$C_1$-$C_6$alkyl-carbonyl-, hetarylcarbonyl-, hetaryl$C_1$-$C_6$alkylcarbonyl-, $C_1$-$C_6$alkyloxy-, aryloxy-, aryl$C_1$-$C_6$alkyloxy-, hetaryloxy-, hetaryl$C_1$-$C_6$alkyloxy-, $C_1$-$C_6$alkyloxy$C_1$-$C_6$alkyl, aryloxy$C_1$-$C_6$alkyl, aryl$C_1$-$C_6$alkyloxy$C_1$-$C_6$alkyl, hetaryl, hetaryl$C_1$-$C_6$alkyl, hetaryloxy$C_1$-$C_6$alkyl, hetaryl$C_1$-$C_6$alkyloxy$C_1$-$C_6$alkyl, —$NR^7R^8$, —$SO_2NR^7R^8$, $NR^7R^8$carbonyl$C_1$-$C_6$alkyl, $R^{11}$carbonylN($R^7$)—, $C_1$-$C_6$alkylS(O)$_n$—, or $R^{12}$S(O)$_n$N($R^7$)—; wherein the aryl and hetaryl groups independently are optionally substituted with one or more $R^{13}$, wherein $R^7$, $R^8$, $R^{11}$, $R^{12}$, $R^{13}$ and n are as defined above.

In another embodiment of the present invention, in formula (I), $R^6$ is halo, hydroxy, oxo, $C_1$-$C_8$alkyl, $C_3$-$C_{10}$cycloalkyl, trihalomethyl, trihalomethyloxy, aryl, aryl$C_1$-$C_6$alkyl, $C_1$-$C_6$alkylcarbonyl-, $C_3$-$C_{10}$cyclo-alkylcarbonyl-, $C_3$-$C_{10}$cycloalkyl$C_1$-$C_6$alkylcarbonyl-, arylcarbonyl-, aryl$C_1$-$C_6$alkyl-carbonyl-, hetarylcarbonyl-, hetaryl$C_1$-$C_6$alkylcarbonyl-, $C_1$-$C_6$alkyloxy-, aryloxy-, aryl$C_1$-$C_6$alkyloxy-, hetaryloxy-, hetaryl$C_1$-$C_6$alkyloxy-, $C_1$-$C_6$alkyloxy$C_1$-$C_6$alkyl, aryloxy$C_1$-$C_6$alkyl, aryl$C_1$-$C_6$alkyloxy$C_1$-$C_6$alkyl, hetaryl, hetaryl$C_1$-$C_6$alkyl, hetaryloxy$C_1$-$C_6$alkyl, hetaryl$C_1$-$C_6$alkyloxy$C_1$-$C_6$alkyl, —$NR^7R^8$, —$SO_2NR^7R^8$, $NR^7R^8$carbonyl$C_1$-$C_6$alkyl, $R^{11}$carbonylN($R^7$)— or $R^{12}$S(O)$_n$N($R^7$)—; wherein the aryl and hetaryl groups independently are optionally substituted with one or more $R^{13}$, wherein $R^7$, $R^8$, $R^{11}$, $R^{12}$, $R^{13}$ and n are as defined above.

In another embodiment of the present invention, in formula (I), $R^6$ is hydrogen, halo, oxo, $C_1$-$C_8$alkyl, trihalomethyl, trihalomethyloxy, aryl, aryl$C_1$-$C_6$alkyl, $C_1$-$C_6$alkylcarbonyl-, $C_3$-$C_{10}$cyclo-alkylcarbonyl-, $C_3$-$C_{10}$cycloalkyl$C_1$-$C_6$alkylcarbonyl-, arylcarbonyl-, aryl$C_1$-$C_6$alkylcarbonyl-, hetarylcarbonyl-, hetaryl$C_1$-$C_6$alkylcarbonyl-, $C_1$-$C_6$alkyloxy-, aryloxy-, aryl$C_1$-$C_6$alkyloxy-, hetaryloxy-, hetaryl$C_1$-$C_6$alkyloxy-, $C_1$-$C_6$alkyloxy$C_1$-$C_6$alkyl, aryloxy$C_1$-$C_6$alkyl, aryl$C_1$-$C_6$alkyloxy$C_1$-$C_6$alkyl, hetaryl, hetaryl$C_1$-$C_6$alkyl, hetaryloxy$C_1$-$C_6$alkyl, hetaryl$C_1$-$C_6$alkyloxy$C_1$-$C_6$alkyl, —$NR^7R^8$ or $NR^7R^8$carbonyl$C_1$-$C_6$alkyl, $R^{11}$carbonylN($R^7$)—, $C_1$-$C_6$alkylS(O)$_n$—; wherein the aryl and hetaryl groups independently are optionally substituted with one or more $R^{13}$, wherein $R^7$, $R^8$, $R^{11}$, $R^{13}$ and n are as defined above.

In another embodiment of the present invention, in formula (I), $R^6$ is hydrogen, halo, oxo, $C_1$-$C_8$alkyl, $C_3$-$C_{10}$cycloalkyl, trihalomethyl, trihalomethyloxy, aryl, aryl$C_1$-$C_6$alkyl, $C_1$-$C_6$alkyloxy-, aryloxy-, aryl$C_1$-$C_6$alkyloxy-, hetaryloxy-, hetaryl$C_1$-$C_6$alkyloxy-, $C_1$-$C_6$alkyloxy$C_1$-$C_6$alkyl, aryloxy$C_1$-$C_6$alkyl, aryl$C_1$-$C_6$alkyloxy$C_1$-$C_6$alkyl, hetaryl, hetaryl$C_1$-$C_6$alkyl, hetaryloxy$C_1$-$C_6$alkyl, hetaryl$C_1$-$C_6$alkyloxy$C_1$-$C_6$alkyl, hetaryl$C_1$-$C_6$alkyloxy$C_1$-$C_6$alkyl, $C_1$-$C_6$alkylS(O)$_n$—; wherein the aryl and hetaryl groups independently are optionally substituted with one or more $R^{13}$, wherein $R^{13}$ is as defined above.

In another embodiment of the present invention, in formula (I), $R^6$ is hydrogen, halo, oxo or $C_1$-$C_8$alkyl.

In another embodiment of the present invention, in formula (I), $R^6$ is halo, oxo or $C_1$-$C_8$alkyl.

In another embodiment of the present invention, in formula (I), $R^6$ is hydrogen.

In another embodiment of the present invention, in formula (I), $R^6$ is $C_1$-$C_6$-alkylS(O)$_n$—.

In another embodiment of the present invention, in formula (I), $R^7$ and $R^8$ independently are $C_3$-$C_{10}$cycloalkyl, $C_3$-$C_{10}$cycloalkyl$C_1$-$C_6$alkyl, $C_3$-$C_{10}$hetcycloalkyl, aryl, hetaryl, aryl$C_1$-$C_6$alkyl or hetaryl$C_1$-$C_6$alkyl wherein the alkyl, aryl and hetaryl groups independently are optionally substituted with one or more of $R^{13}$, wherein $R^{13}$ is as defined above.

In another embodiment of the present invention, in formula (I), $R^7$ and $R^8$ independently are $C_3$-$C_{10}$cycloalkyl, $C_3$-$C_{10}$cycloalkyl$C_1$-$C_6$alkyl, $C_3$-$C_{10}$hetcycloalkyl, aryl$C_1$-$C_6$alkyl or hetaryl$C_1$-$C_6$alkyl wherein the alkyl, aryl and hetaryl groups independently are optionally substituted with one or more of $R^{13}$, wherein $R^{13}$ is as defined above.

In another embodiment of the present invention, in formula (I), $R^7$ and $R^8$ independently are $C_3$-$C_{10}$cycloalkyl$C_1$-$C_6$alkyl, $C_3$-$C_{10}$hetcycloalkyl, aryl$C_1$-$C_6$alkyl or hetaryl$C_1$-$C_6$alkyl wherein the alkyl, aryl and hetaryl groups independently are optionally substituted with one or more of $R^{13}$, wherein $R^{13}$ is as defined above.

In another embodiment of the present invention, in formula (I), $R^7$ and $R^8$ together with the nitrogen to which they are attached, are forming a saturated or partially saturated cyclic or bicyclic ring system containing from 4 to 12 carbon atoms and from 0 to 2 additional heteroatoms selected from nitrogen or oxygen, the ring system optionally being substituted with at least one or more $R^{13}$, wherein $R^{13}$ is as defined above.

In another embodiment of the present invention, in formula (I), $R^7$ and $R^8$ together with the nitrogen to which they are attached, are forming a saturated or partially saturated cyclic or bicyclic ring system containing from 6 to 10 carbon atoms and from 0 to 2 additional heteroatoms selected from nitrogen or oxygen, the ring system optionally being substituted with at least one or more $R^{13}$, wherein $R^{13}$ is as defined above.

In another embodiment of the present invention, in formula (I), $R^7$ and $R^8$ together with the nitrogen to which they are attached, are forming a saturated or partially saturated cyclic or bicyclic ring system containing from 6 to 10 carbon atoms and from 1 to 2 additional heteroatoms selected from nitrogen or oxygen, the ring system optionally being substituted with at least one or more $R^{13}$, wherein $R^{13}$ is as defined above.

In another embodiment of the present invention, in formula (I), $R^9$ is $C_3$-$C_{10}$cycloalkyl, $C_3$-$C_{10}$cycloalkyl$C_1$-$C_6$alkyl, $C_3$-$C_{10}$hetcycloalkyl-, $C_3$-$C_{10}$cycloalkylcarbonyl-, $C_3$-$C_{10}$hetcycloalkylcarbonyl-, arylcarbonyl-, hetarylcarbonyl-, $C_1$-$C_6$alkyloxy, aryloxy, aryl$C_1$-$C_6$-alkyloxy, $C_3$-$C_{10}$cycloalkyloxy, $C_3$-$C_{10}$hetcycloalkyloxy-, $C_1$-$C_6$alkyloxy$C_1$-$C_6$alkyl, $NR^7R^8$-carbonyl$C_1$-$C_6$alkyl-, $C_1$-$C_6$alkylS(O)$_n$—, arylS(O)$_n$—, aryl$C_1$-$C_6$alkylS(O)$_n$—, aryl$C_1$-$C_6$alkyl or hetaryl$C_1$-$C_6$alkyl; wherein the aryl and hetaryl groups independently are optionally substituted with one or more $R^{11}$, wherein $R^7$, $R^8$, $R^{11}$ and n are as defined above.

In another embodiment of the present invention, in formula (I), $R^9$ is $C_3$-$C_{10}$cycloalkyl, $C_3$-$C_{10}$cycloalkyl$C_1$-$C_6$alkyl, $C_3$-$C_{10}$hetcycloalkyl-, $C_1$-$C_6$alkyloxy, aryloxy, aryl$C_1$-$C_6$- alkyloxy, $C_3$-$C_{10}$cycloalkyloxy, $C_3$-$C_{10}$hetcycloalkyloxy-, $C_1$-$C_6$alkyloxy$C_1$-$C_6$alkyl, $NR^7R^8$-carbonyl$C_1$-$C_6$alkyl-, $C_1$-$C_6$alkylS(O)$_n$—, arylS(O)$_n$— or aryl$C_1$-$C_6$alkylS(O)$_n$—; wherein the aryl and hetaryl groups independently are optionally substituted with one or more $R^{11}$, wherein $R^7$, $R^8$, $R^{11}$ and n are as defined above.

In another embodiment of the present invention, in formula (I), $R^9$ is $C_3$-$C_{10}$cycloalkyl, $C_3$-$C_{10}$cycloalkyl$C_1$-$C_6$alkyl, $C_3$-$C_{10}$hetcycloalkyl-, $C_1$-$C_6$alkyloxy, aryloxy, aryl$C_1$-$C_6$-alkyloxy, $C_3$-$C_{10}$cycloalkyloxy, $C_3$-$C_{10}$hetcycloalkyloxy-, $C_1$-$C_6$alkyloxy$C_1$-$C_6$alkyl or $NR^7R^8$-carbonyl$C_1$-$C_6$alkyl-; wherein the aryl and hetaryl groups independently are optionally substituted with one or more $R^{11}$, wherein $R^7$, $R^8$ and $R^{11}$ are as defined above.

In another embodiment of the present invention, in formula (I), $R^{10}$ is hydroxy, $C_1$-$C_8$alkyloxy or —$NR^7R^8$, wherein $R^7$ and $R^8$ are as defined above.

In another embodiment of the present invention, in formula (I), $R^{10}$ is hydroxy or $C_1$-$C_8$alkyloxy.

In another embodiment of the present invention, in formula (I), $R^{10}$ is —$NR^7R^8$ wherein $R^7$ and $R^8$ are as defined above.

In another embodiment of the present invention, in formula (I), $R^{11}$ is $C_1$-$C_6$alkyl, aryl, aryl$C_1$-$C_6$alkyl, hetaryl, hetaryl$C_1$-$C_6$alkyl, $C_3$-$C_{10}$cycloalkyl, $C_3$-$C_{10}$hetcycloalkyl, $C_1$-$C_6$alkyloxy-, aryloxy-, aryl$C_1$-$C_6$alkyloxy-, hetaryloxy-, hetaryl$C_1$-$C_6$alkyloxy-, aryl$C_1$-$C_6$alkyloxy$C_1$-$C_6$-alkyl-, hetaryl$C_1$-$C_6$alkyloxy$C_1$-$C_6$alkyl- or $R^7R^8NC_1$-$C_6$alkyl- wherein the alkyl, alkenyl, cycloalkyl, hetcycloalkyl, aryl and hetaryl groups are optionally substituted with $R^{14}$, wherein $R^7$, $R^8$ and $R^{14}$ are as defined above.

In another embodiment of the present invention, in formula (I), $R^{11}$ is $C_1$-$C_6$alkyl, aryl, hetaryl, $C_3$-$C_{10}$cycloalkyl, $C_3$-$C_{10}$hetcycloalkyl, $C_1$-$C_6$alkyloxy-, aryloxy-, aryl$C_1$-$C_6$alkyloxy-, hetaryloxy-, hetaryl$C_1$-$C_6$alkyloxy- or $R^7R^8NC_1$-$C_6$alkyl- wherein the alkyl, alkenyl, cycloalkyl, hetcycloalkyl, aryl and hetaryl groups are optionally substituted with $R^{14}$, wherein $R^7$, $R^8$ and $R^{14}$ are as defined above.

In another embodiment of the present invention, in formula (I), $R^{11}$ is aryl, hetaryl, $C_3$-$C_{10}$cycloalkyl, $C_1$-$C_6$alkyloxy-, aryloxy-, hetaryloxy, or $R^7R^8NC_1$-$C_6$alkyl- wherein the alkyl, alkenyl, cycloalkyl, hetcycloalkyl, aryl and hetaryl groups are optionally substituted with $R^{14}$, wherein $R^7$, $R^8$ and $R^{14}$ are as defined above.

In another embodiment of the present invention, in formula (I), $R^{12}$ is $C_1$-$C_6$alkyl, $C_3$-$C_{10}$cycloalkyl, aryl$C_1$-$C_6$alkyl, hetaryl or hetaryl$C_1$-$C_6$alkyl.

In another embodiment of the present invention, in formula (I), $R^{12}$ is $C_3$-$C_{10}$cycloalkyl, aryl$C_1$-$C_6$alkyl or hetaryl$C_1$-$C_6$alkyl.

In another embodiment of the present invention, in formula (I), $R^{12}$ is $C_1$-$C_6$alkyl, $C_3$-$C_{10}$cycloalkyl or aryl$C_1$-$C_6$alkyl.

In another embodiment of the present invention, in formula (I), $R^{13}$ is $R^3$, oxo, $C_1$-$C_6$alkyl, $C_3$-$C_{10}$cycloalkyl, $C_3$-$C_{10}$hetcycloalkyl, aryl or hetaryl, wherein the alkyl, cycloalkyl, hetcycloalkyl, aryl and hetaryl groups independently are optionally substituted with one or more of $R^{15}$, wherein $R^3$ and $R^{15}$ are as defined above.

In another embodiment of the present invention, in formula (I), $R^{13}$ is $R^3$, oxo, $C_3$-$C_{10}$cycloalkyl, $C_3$-$C_{10}$hetcycloalkyl or aryl, hetaryl, wherein the cycloalkyl, hetcycloalkyl, aryl and hetaryl groups independently are optionally substituted with one or more of $R^{15}$, wherein $R^3$ and $R^{15}$ are as defined above.

In another embodiment of the present invention, in formula (I), $R^{13}$ is $R^3$ or oxo, wherein $R^3$ is as defined above, In another embodiment of the present invention, in formula (I), $R^{14}$ is hydrogen, halo, hydroxy, oxo, cyano, $C_1$-$C_8$alkyl, —$NR^7R^8$, $C_1$-$C_6$alkyloxy or aryl$C_1$-$C_6$alkyl, wherein $R^3$ and $R^{15}$ are as defined above.

In another embodiment of the present invention, in formula (I), $R^{14}$ is hydrogen, halo, hydroxy, oxo, $C_1$-$C_8$alkyl, $C_1$-$C_6$alkyloxy or aryl$C_1$-$C_6$alkyl.

In another embodiment of the present invention, in formula (I), $R^{14}$ is hydrogen, halo, hydroxy, oxo, $C_1$-$C_6$alkyloxy or aryl$C_1$-$C_6$alkyl.

In another embodiment of the present invention, in formula (I), $R^{15}$ is $C_1$-$C_8$alkyl or $C_1$-$C_6$alkyloxy.

In another embodiment of the present invention, in formula (I), $R^{17}$ and $R^{18}$ independently are hydrogen, hydroxy, cyano, $C_1$-$C_8$alkyl, trihalomethyl, trihalomethyloxy, aryl, aryl$C_1$-$C_6$alkyl, —$COR^{10}$, $C_1$-$C_6$alkyloxy-, aryloxy-, aryl$C_1$-$C_6$alkyloxy-, hetaryloxy-, hetaryl$C_1$-$C_6$alkyloxy-, hetaryl, hetaryl$C_1$-$C_6$alkyl, hetaryloxy$C_1$-$C_6$alkyl, hetaryl$C_1$-$C_6$alkyloxy$C_1$-$C_6$alkyl, —$NR^7R^8$, —$SO_2NR^7R^8$, $NR^7R^8$-carbonyl$C_1$-$C_6$alkyl, $R^{11}$carbonylN($R^7$)—, arylS(O)$_n$—, hetarylS(O)$_n$— or $R^{12}$S(O)$_n$N($R^7$)—; wherein the aryl and hetaryl groups independently are optionally substituted with one or more $R^{13}$, wherein $R^7$, $R^8$, $R^{11}$, $R^{12}$, $R^{13}$ and n are as defined above.

In another embodiment of the present invention, in formula (I), $R^{17}$ and $R^{18}$ independently are hydrogen, hydroxy, cyano, $C_1$-$C_8$alkyl, trihalomethyl, trihalomethyloxy, aryl, aryl$C_1$-$C_6$alkyl, $C_1$-$C_6$alkyloxy-, aryloxy-, aryl$C_1$-$C_6$alkyloxy-, hetaryloxy-, —$SO_2NR^7R^8$, $NR^7R^8$carbonyl$C_1$-$C_6$alkyl, $R^{11}$carbonylN($R^7$)—, arylS(O)$_n$—, hetarylS(O)$_n$— or $R^{12}$S(O)$_n$N($R^7$)—; wherein the aryl and hetaryl groups independently are optionally substituted with one or more $R^{13}$, wherein $R^7$, $R^8$, $R^{11}$, $R^{12}$, $R^{13}$ and n are as defined above.

In another embodiment of the present invention, in formula (I), $R^{17}$ and $R^{18}$ independently are hydrogen, hydroxy, cyano, $C_1$-$C_8$alkyl, trihalomethyl, trihalomethyloxy, aryl, aryl$C_1$-$C_6$alkyl, $C_1$-$C_6$alkyloxy-, aryloxy-, aryl$C_1$-$C_6$alkyloxy- or hetaryloxy; wherein the aryl and hetaryl groups independently are optionally substituted with one or more $R^{13}$ wherein $R^{13}$ is as defined above.

In another embodiment of the present invention, in formula (I), $R^{17}$ and $R^{18}$ together with the carbon atom to which they are attached are —C(=O)—.

In another embodiment of the present invention, in formula (I), n is 1.

In another embodiment of the present invention, in formula (I), n is 2.

In another embodiment of the present invention, in formula (I), p is 1.

In another embodiment of the present invention, in formula (I), p is 2.

In another embodiment of the present invention, in formula (I), is selected from:

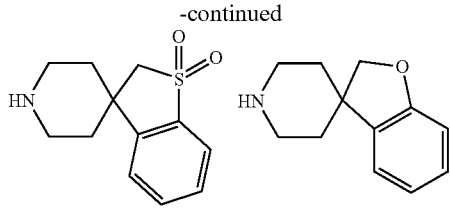
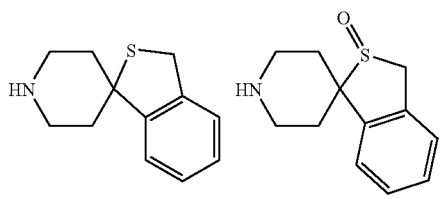
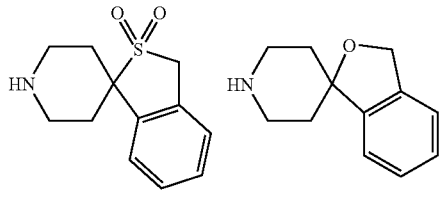
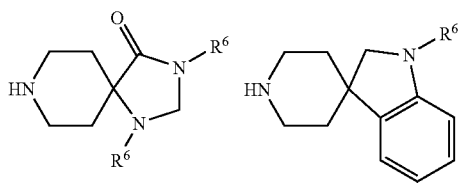
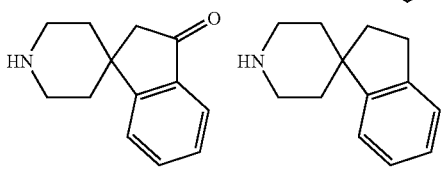
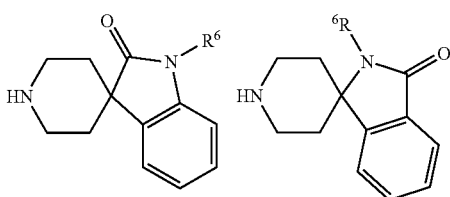
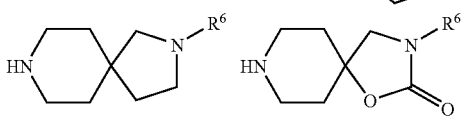
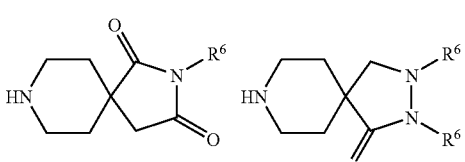
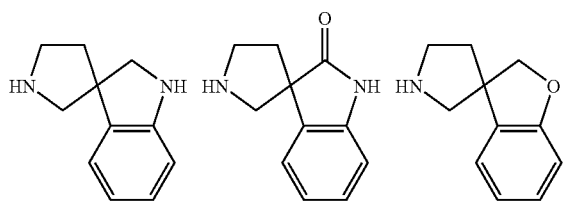
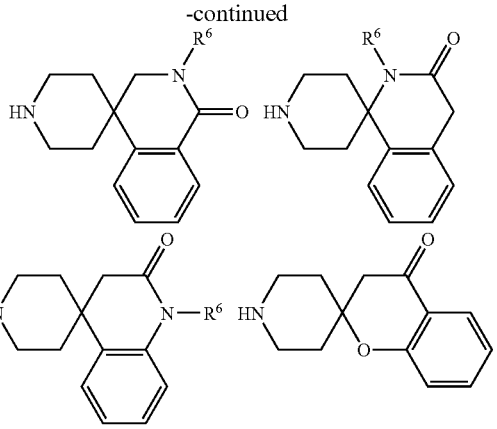
wherein $R^G$ is as defined above.
In another embodiment of the present invention, in formula (I),
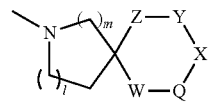
is selected from:
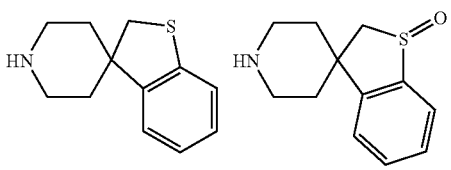
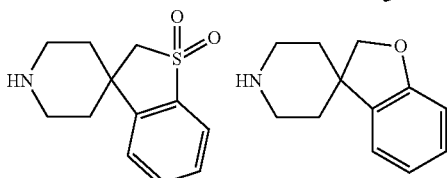
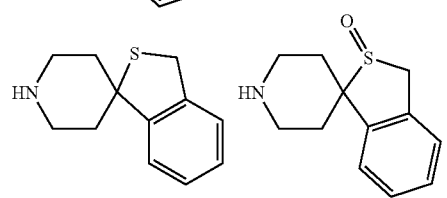
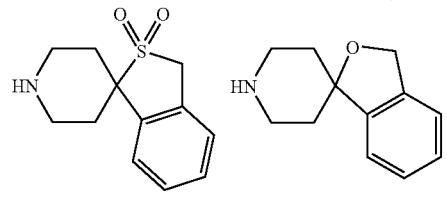
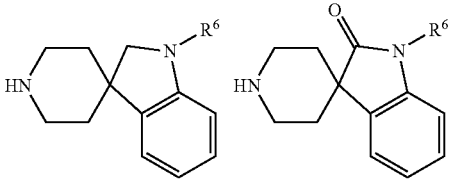

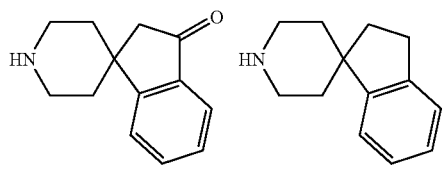

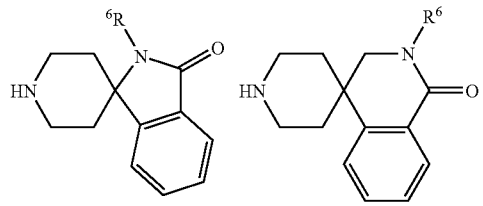

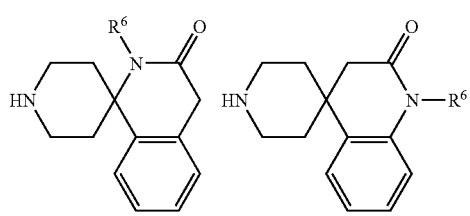

wherein R⁶ is as defined above.

In another embodiment of the present invention, in formula (I),

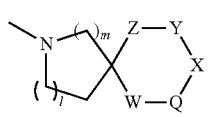

is selected from:

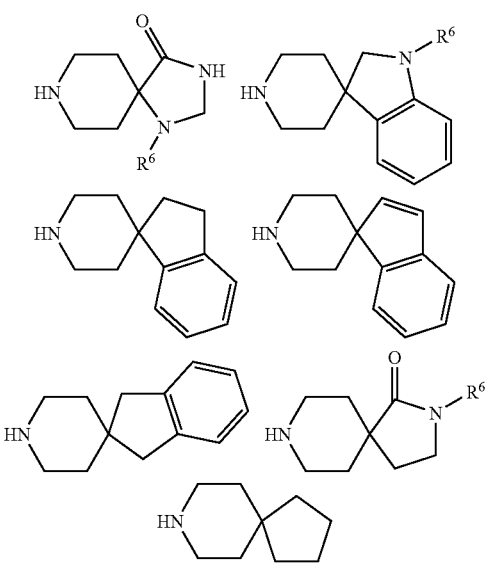

In another embodiment of the present invention, in formula (I),

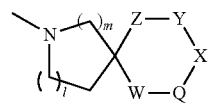

is selected from:

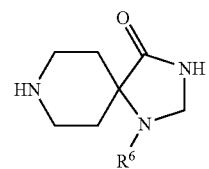

In another embodiment of the present invention, in formula (I),

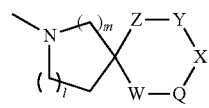

is selected from:

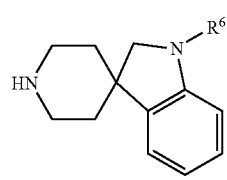

In another embodiment of the present invention, in formula (I),

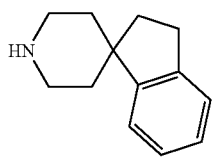

is selected from:

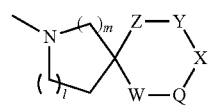

In another embodiment of the present invention, in formula (I), is selected from:

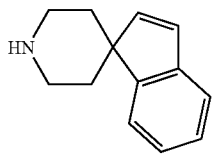

In another embodiment of the present invention, in formula (I),

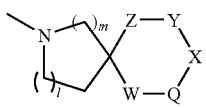

is selected from:

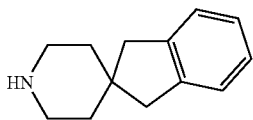

In another embodiment of the present invention, in formula (I),

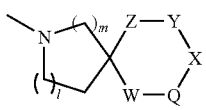

is selected from:

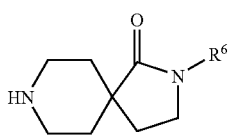

In another embodiment of the present invention, in formula (I),

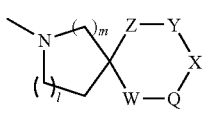

is selected from:

In another embodiment of the present invention, the compounds of the general formula (I) or a prodrug thereof is selected from the group of compounds of examples 1 and 2:

1H-Indole-5-carbonyl)-1-phenyl-1,3,8-triaza-spiro[4.5]decan-4-one;
3,4-Dihydrospiro(1H-indene-1,4'-piperidin-1-yl)-(1H-indol-5-yl)-methanone;
Spiro(1H-indene-1,4'-piperidin-1-yl)-(3-N,N-dimethylamino-phenyl)-methanone;
Spiro(1H-indene-1,4'-piperidin-1-yl)-(1H-benzimidazol-5-yl)-methanone;
2,3-Dihydrospiro(1-methanesulfonyl-indol-3,4'-piperidin-1-yl)-(1H-indol-5-yl)-methanone;
2,3-Dihydrospiro(1-methanesulfonyl-indol-3,4'-piperidin-1-yl)-(3-N,N-dimethylamino-phenyl)-methanone;
Spiro(1H-indene-1,4'-piperidin-1-yl)-(4-(2,4-dihydro-5-methyl-pyrazol-2-yl-3-one)phenyl)-methanone;
Spiro(1H-indene-1,4'-piperidin-1-yl)-(4-(imidazole-1-yl)phenyl)-methanone;
Spiro(cyclopentane-1,4'-piperidin-1-yl)-(1H-benzimidazol-5-yl)-methanone;
2,3-Dihydrospiro(1H-indene-1,4'-piperidin-1-yl)-(4-N,N-dimethylamino-phenyl)-methanone;
Spiro(1H-indene-1,4'-piperidin-1-yl)-(4-N,N-dimethylamino-phenyl)-methanone;
2,3-Dihydrospiro(1H-indene-1,4'-piperidin-1-yl)-(1H-benzimidazol-5-yl)-methanone;
2,3-Dihydrospiro(1-methanesulfonyl-indol-3,4'-piperidin-1-yl)-(benzimidazol-5-yl)-methanone;
1,3-Dihydrospiro(1H-indene-2,4'-piperidin-1-yl)-(4-N,N-dimethylamino-phenyl)-methanone;
Spiro(1-tert-butyl-pyrrolidin-2-one-3,4'-piperidin-1-yl)-(4-N,N-dimethylamino-phenyl)-methanone; or
a salt thereof with a pharmaceutically acceptable acid or base, or any optical isomer or mixture of optical isomers, including a racemic mixture, or any tautomeric forms.

In another embodiment of the present invention, the compounds of the general formula (I) or a prodrug thereof is selected from the group of compounds of examples 1 and 2, or salt thereof with a pharmaceutically acceptable acid or base, or any optical isomer or mixture of optical isomers, including a racemic mixture, or any tautomeric forms.

The compounds of the present invention have asymmetric centers and may occur as racemates, racemic mixtures, and as individual enantiomers or diastereoisomers, with all isomeric forms being included in the present invention as well as mixtures thereof.

The present invention also encompasses pharmaceutically acceptable salts of the present compounds. Such salts include pharmaceutically acceptable acid addition salts, pharmaceutically acceptable base addition salts, pharmaceutically acceptable metal salts, ammonium and alkylated ammonium salts. Acid addition salts include salts of inorganic acids as well as organic acids. Representative examples of suitable inorganic acids include hydrochloric, hydrobromic, hydroiodic, phosphoric, sulfuric, nitric acids and the like. Representative examples of suitable organic acids include formic, acetic, trichloroacetic, trifluoroacetic, propionic, benzoic, cinnamic, citric, fumaric, glycolic, lactic, maleic, malic, malonic, mandelic, oxalic, picric, pyruvic, salicylic, succinic, methanesulfonic, ethanesulfonic, tartaric, ascorbic, pamoic, bismethylene salicylic, ethanedisulfonic, gluconic, citraconic, aspartic, stearic, palmitic, EDTA, glycolic, p-aminobenzoic, glutamic, benzenesulfonic, p-toluenesulfonic acids, sulphates, nitrates, phosphates, perchlorates, borates, acetates, benzoates, hydroxynaphthoates, glycerophosphates, ketoglutarates and the like. Further examples of pharmaceutically acceptable inorganic or organic acid addition salts include the pharmaceutically acceptable salts listed in J. Pharm. Sci., 66, 2 (1977), which is incorporated herein by reference. Examples of metal salts include lithium, sodium, potassium, barium, calcium, magnesium, zinc, calcium salts and the like. Examples of amines and organic amines include ammonium, methylamine, dimethylamine, trimethylamine, ethylamine, diethylamine, propylamine, butylamine, tetramethylamine, ethanolamine, diethanolamine, triethanolamine, meglumine, ethylenediamine, choline, N,N'-dibenzylethylenediamine, N-benzylphenylethylamine, N-methyl-D-glucamine, guanidine and the like. Examples of cationic amino acids include lysine, arginine, histidine and the like.

Further, some of the compounds of the present invention may form solvates with water or common organic solvents. Such solvates are encompassed within the scope of the invention.

The pharmaceutically acceptable salts are prepared by reacting a compound of the present invention with 1 to 4 equivalents of a base such as sodium hydroxide, sodium methoxide, sodium hydride, potassium tert-butoxide, calcium hydroxide, magnesium hydroxide and the like, in solvents like ether, THF, methanol, tert-butanol, dioxane, isopropanol, ethanol etc. Mixtures of solvents may be used. Organic bases like lysine, arginine, diethanolamine, choline, guandine and their derivatives etc. may also be used. Alternatively, acid addition salts wherever applicable are prepared by treatment with acids such as hydrochloric acid, hydrobromic acid, nitric acid, sulfuric acid, phosphoric acid, p-toluenesulphonic acid, methanesulfonic acid, acetic acid, citric acid, maleic acid salicylic acid, hydroxynaphthoic acid, ascorbic acid, palmitic acid, succinic acid, benzoic acid, benzenesulfonic acid, tartaric acid and the like in solvents like ethyl acetate, ether, alcohols, acetone, THF, dioxane etc. Mixture of solvents may also be used.

The stereoisomers of the compounds forming part of this invention may be prepared by using reactants in their single enantiomeric form in the process wherever possible or by conducting the reaction in the presence of reagents or catalysts in their single enantiomer form or by resolving the mixture of stereoisomers by conventional methods. Some of the preferred methods include use of microbial resolution, enzymatic resolution, resolving the diastereomeric salts formed with chiral acids such as mandelic acid, camphorsulfonic acid, tartaric acid, lactic acid, and the like wherever applicable or chiral bases such as brucine, (R)- or (S)-phenylethylamine, cinchona alkaloids and their derivatives and the like. Commonly used methods are compiled by Jaques et al. in "Enantiomers, Racemates and Resolution" (Wiley Interscience, 1981). More specifically the compound of the present invention may be converted to a 1:1 mixture of diastereomeric amides by treating with chiral amines, aminoacids, aminoalcohols derived from aminoacids; conventional reaction conditions may be employed to convert acid into an amide; the diastereomers may be separated either by fractional crystallization or chromatography and the stereoisomers of compound of formula I may be prepared by hydrolysing the pure diastereomeric amide.

Various polymorphs of the compounds forming part of this invention may be prepared by crystallization of said compounds under different conditions; for example, using different solvents commonly used or their mixtures for recrystallization; crystallizations at different temperatures; or various modes of cooling, ranging from very fast to very slow cooling during crystallizations. Polymorphs may also be obtained by heating or melting the compound followed by gradual or fast cooling. The presence of polymorphs may be determined by solid probe nmr spectroscopy, ir spectroscopy, differential scanning calorimetry, powder X-ray diffraction or such other techniques.

The invention also encompasses prodrugs of the present compounds, which on administration undergo chemical conversion by metabolic processes before becoming active pharmacological substances. In general, such prodrugs will be functional derivatives of the present compounds, which are readily convertible in vivo into the required compound of the present invention. Conventional procedures for the selection and preparation of suitable prodrug derivatives are described, for example, in "Design of Prodrugs", ed. H. Bundgaard, Elsevier, 1985.

It is a well known problem in drug discovery that compounds, such as enzyme inhibitors, may be very potent and selective in biochemical assays, yet be inactive in vivo. This lack of so-called bioavailability may be ascribed to a number of different factors such as lack of or poor absorption in the gut, first pass metabolism in the liver and/or poor uptake in cells. Although the factors determining bioavailability are not completely understood, there are many examples in the scientific literature—well known to those skilled in the art—of how to modify compounds, which are potent and selective in biochemical assays but show low or no activity in vivo, into drugs that are biologically active.

It is within the scope of the invention to modify the compounds of the present invention, termed the 'original compound', by attaching chemical groups that will improve the bioavailability of said compounds in such a way that the uptake in cells or mammals is facilitated.

Examples of said modifications, which are not intended in any way to limit the scope of the invention, include changing of one or more carboxy groups to esters (for instance methyl esters, ethyl esters, tert-butyl, acetoxymethyl, pivaloyloxymethyl esters or other acyloxymethyl esters). Compounds of the invention, original compounds, such modified by attaching chemical groups are termed 'modified compounds'.

The invention also encompasses active metabolites of the present compounds.

The compounds according to the invention alter, and more specifically, reduce the level of active intracellular glucocorticoid and are accordingly useful for the treatment, prevention and/or prophylaxis of disorders and diseases in which such a modulation or reduction is beneficial.

Accordingly, the present compounds may be applicable for the treatment, prevention and/or prophylaxis of the metabolic syndrome, insulin resistance, dyslipidemia, hypertension, obesity, type 2 diabetes, impaired glucose tolerance (IGT), impaired fasting glucose (IFG) Latent Autoimmune Diabetes in the Adult (LADA), type 1 diabetes, diabetic late complications including cardiovascular diseases, cardiovascular disorders, disorders of lipid metabolism, neurodegenerative and psychiatric disorders, dysregulation of intraocular pressure including glaucoma, immune disorders, inappropriate immune responses, musculo-skeletal disorders, gastrointestinal disorders, polycystic ovarie syndrome (PCOS), reduced hair growth or other diseases, disorders or conditions that are influenced by intracellular glucocorticoid levels, adverse effects of increased blood levels of active endogenous or exogenous glucocorticoid, and any combination thereof, adverse effects of increased plasma levels of endogenous active glucocorticoid, Cushing's disease, Cushing's syndrome, adverse effects of glucocorticoid receptor agonist treatment of autoimmune diseases, adverse effects of glucocorticoid receptor agonist treatment of inflammatory diseases, adverse effects of glucocorticoid receptor agonist treatment of diseases with an inflammatory component, adverse effects of glucocorticoid receptor agonist treatment as a part of cancer chemotherapy, adverse effects of glucocorticoid receptor agonist treatment for surgical/post-surgical or other trauma, adverse effects of glucocorticoid receptor agonist therapy in the context of organ or tissue transplantation or adverse effects of glucocorticoid receptor agonist treatment in other diseases, disorders or conditions where glucocorticoid receptor agonists provide clinically beneficial effects.

More specifically the present compounds may be applicable for the treatment, prevention and/or prophylaxis of the metabolic syndrome, type 2 diabetes, diabetes as a consequence of obesity, insulin resistance, hyperglycemia, prandial hyperglycemia, hyperinsulinemia, inappropriately low insulin secretion, impaired glucose tolerance (IGT), impaired fasting glucose (IFG), increased hepatic glucose production, type 1 diabetes, LADA, pediatric diabetes, dyslipidemia, diabetic dyslipidemia, hyperlipidemia, hypertriglyceridemia, hyperlipoproteinemia, hypercholesterolemia, decreased HDL cholesterol, impaired LDL/HDL ratio, other disorders of lipid metabolism, obesity, visceral obesity, obesity as a consequence of diabetes, increased food intake, hypertension, diabetic late complications, micro-/macroalbuminuria, nephropathy, retinopathy, neuropathy, diabetic ulcers, cardiovascular diseases, arteriosclerosis, atherosclerosis, coronary artery disease, cardiac hypertrophy, myocardial ischemia, heart insufficiency, congestional heart failure, stroke, myocardial infarction, arrythmia, decreased blood flow, erectile dysfunction (male or female), myopathy, loss of muscle tissue, muscle wasting, muscle catabolism, osteoporosis, decreased linear growth, neurodegenerative and psychiatric disorders, Alzheimers disease, neuronal death, impaired cognitive function, depression, anxiety, eating disorders, appetite regulation, migraine, epilepsia, addiction to chemical substances, disorders of intraocular pressure, glaucoma, polycystic ovary syndrome (PCOS), inappropriate immune responses, inappropriate T helper-1/T helper-2 polarisation, bacterial infections, mycobacterial infections, fungal infections, viral infections, parasitic infestations, suboptimal responses to immunizations, immune dysfunction, partial or complete baldness, or diseases, disorders or conditions that are influenced by intracellular glucocorticoid levels and any combination thereof, adverse effects of glucocorticoid receptor agonist treatment of allergic-inflammatory diseases such as asthma and atopic dermatitis, adverse effects of glucocorticoid receptor agonist treatment of disorders of the respiratory system e.g. asthma, cystic fibrosis, emphysema, bronchitis, hypersensitivity, pneumonitis, eosinophilic pneumonias, pulmonary fibrosis, adverse effects of glucocorticoid receptor agonist treatment of inflammatory bowel disease such as Crohn's disease and ulcerative colitis; adverse effects of glucocorticoid receptor agonist treatment of disorders of the immune system, connective tissue and joints e.g. reactive arthritis, rheumatoid arthritis, Sjögren's syndrome, systemic lupus erythematosus, lupus nephritis, Henoch-Schönlein purpura, Wegener's granulomatosis, temporal arteritis, systemic sclerosis, vasculitis, sarcoidosis, dermatomyositis-polymyositis, pemphigus vulgaris; adverse effects of glucocorticoid receptor agonist treatment of endocrinological diseases such as hyperthyroidism, hypoaldosteronism, hypopituitarism; adverse effects of glucocorticoid receptor agonist treatment of hematological diseases e.g. hemolytic anemia, thrombocytopenia, paroxysmal nocturnal hemoglobinuria; adverse effects of glucocorticoid receptor agonist treatment of cancer such as spinal cord diseases, neoplastic compression of the spinal cord, brain tumours, acute lymphoblastic leukemia, Hodgkin's disease, chemotherapy-induced nausea, adverse effects of glucocorticoid receptor agonist treatment of diseases of muscle and at the neuro-muscular joint e.g. myasthenia gravis and hereditary myopathies (e.g. Duchenne muscular dystrophy), adverse effects of glucocorticoid receptor agonist treatment in the context of surgery & transplantation e.g. trauma, post-surgical stress, surgical stress, renal transplantation, liver transplantation, lung transplantation, pancreatic islet transplantation, blood stem cell transplantation, bone marrow transplantation, heart transplantation, adrenal gland transplantation, tracheal transplantation, intestinal transplantation, corneal transplantation, skin grafting, keratoplasty, lens implantation and other procedures where immunosuppression with glucocorticoid receptor agonists is beneficial; adverse effects of glucocorticoid receptor agonist treatment of brain absess, nausea/vomiting, infections, hypercalcemia, adrenal hyperplasia, autoimmune hepatitis, spinal cord diseases, saccular aneurysms or adverse effects to glucocorticoid receptor agonist treatment in other diseases, disorders and conditions where glucocorticoid receptor agonists provide clinically beneficial effects.

Accordingly, in a further aspect the invention relates to a compound according to the invention for use as a pharmaceutical composition.

The invention also relates to pharmaceutical compositions comprising, as an active ingredient, at least one compound according to the invention together with one or more pharmaceutically acceptable carriers or diluents.

The pharmaceutical composition is preferably in unit dosage form, comprising from about 0.05 mg/day to about 2000 mg/day, preferably from about 1 mg/day to about 500 mg/day of a compound according to the invention.

In another embodiment, the patient is treated with a compound according to the invention for at least about 1 week, for at least about 2 weeks, for at least about 4 weeks, for at least about 2 months or for at least about 4 months.

In yet another embodiment, the pharmaceutical composition is for oral, nasal, transdermal, pulmonal or parenteral administration.

Furthermore, the invention relates to the use of a compound according to the invention for the preparation of a pharmaceutical composition for the treatment, prevention and/or prophylaxis of disorders and diseases wherein a modulation or an inhibition of the activity of 11βHSD1 is beneficial.

The invention also relates to a method for the treatment, prevention and/or prophylaxis of disorders and diseases wherein a modulation or an inhibition of the activity of 11βHSD1 is beneficial, the method comprising administering to a subject in need thereof an effective amount of a compound according to the invention.

In a preferred embodiment of the invention the present compounds are used for the preparation of a medicament for the treatment, prevention and/or prophylaxis of any diseases and conditions that are influenced by intracellular glucocorticoid levels as mentioned above.

Thus, in a preferred embodiment of the invention the present compounds are used for the preparation of a medicament for the treatment, prevention and/or prophylaxis of conditions and disorders where a decreased level of active intracellular glucocorticoid is desirable, such as the conditions and diseases mentioned above.

In yet a preferred embodiment of the invention the present compounds are used for the preparation of a medicament for the treatment, prevention and/or prophylaxis of the metabolic syndrome including insulin resistance, dyslipidemia, hypertension and obesity.

In yet another preferred embodiment of the invention the present compounds are used for the preparation of a medicament for the treatment, prevention and/or prophylaxis of type 2 diabetes, impaired glucose tolerance (IGT), impaired fasting glucose (IFG).

In yet another preferred embodiment of the invention the present compounds are used for the preparation of a pharmaceutical composition for the delaying or prevention of the progression from IGT to type 2 diabetes.

In yet another preferred embodiment of the invention the present compounds are used for the preparation of a pharmaceutical composition for the delaying or prevention of the progression of the metabolic syndrome into type 2 diabetes.

In still another preferred embodiment of the invention the present compounds are used for the preparation of a pharmaceutical composition for the treatment, prevention and/or prophylaxis of diabetic late complications including cardiovascular diseases; arteriosclerosis; atherosclerosis.

In a further preferred embodiment of the invention the present compounds are used for the preparation of a pharmaceutical composition for the treatment, prevention and/or prophylaxis of neurodegenerative and psychiatric disorders.

In yet a further preferred embodiment of the invention the present compounds are used for the preparation of a pharmaceutical composition for the treatment, prevention and/or prophylaxis of adverse effects of glucocorticoid receptor agonist treatment or therapy.

In another embodiment of the present invention, the route of administration may be any route which effectively transports a compound according to the invention to the appropriate or desired site of action, such as oral, nasal, buccal, transdermal, pulmonal, or parenteral.

In still a further aspect of the invention the present compounds are administered in combination with one or more further active substances in any suitable ratios. Such further active substances may e.g. be selected from antiobesity agents, antidiabetics, agents modifying the lipid metabolism, antihypertensive agents, glucocorticoid receptor agonists, agents for the treatment and/or prevention of complications resulting from or associated with diabetes and agents for the treatment and/or prevention of complications and disorders resulting from or associated with obesity.

Thus, in a further aspect of the invention the present compounds may be administered in combination with one or more antiobesity agents or appetite regulating agents.

Such agents may be selected from the group consisting of CART (cocaine amphetamine regulated transcript) agonists, NPY (neuropeptide Y) antagonists, MC4 (melanocortin 4) agonists, orexin antagonists, TNF (tumor necrosis factor) agonists, CRF (corticotropin releasing factor) agonists, CRF BP (corticotropin releasing factor binding protein) antagonists, urocortin agonists, β3 agonists, MSH (melanocyte-stimulating hormone) agonists, MCH (melanocyte-concentrating hormone) antagonists, CCK (cholecystokinin) agonists, serotonin re-uptake inhibitors, serotonin and noradrenaline re-uptake inhibitors, mixed serotonin and noradrenergic compounds, 5HT (serotonin) agonists, bombesin agonists, galanin antagonists, growth hormone, growth hormone releasing compounds, TRH (thyreotropin releasing hormone) agonists, UCP 2 or 3 (uncoupling protein 2 or 3) modulators, leptin agonists, DA agonists (bromocriptin, doprexin), lipase/amylase inhibitors, PPAR (peroxisome proliferator-activated receptor) modulators, RXR (retinoid X receptor) modulators, TR β agonists, AGRP (Agouti related protein) inhibitors, H3 histamine antagonists, opioid antagonists (such as naltrexone), exendin-4, GLP-1 and ciliary neurotrophic factor.

In one embodiment of the invention the antiobesity agent is leptin; dexamphetamine or amphetamine; fenfluramine or dexfenfluramine; sibutramine; orlistat; mazindol or phentermine.

Suitable antidiabetic agents include insulin, insulin analogues and derivatives such as those disclosed in EP 792 290 (Novo Nordisk A/S), e.g. $N^{\epsilon B29}$-tetradecanoyl des (B30) human insulin, EP 214 826 and EP 705 275 (Novo Nordisk A/S), e.g. $Asp^{B28}$ human insulin, U.S. Pat. No. 5,504,188 (Eli Lilly), e.g. $LYS^{B28}$ $Pro^{B29}$ human insulin, EP 368 187 (Aventis), e.g. Lantus, which are all incorporated herein by reference, GLP-1 (glucagon like peptide-1) and GLP-1 derivatives such as those disclosed in WO 98/08871 to Novo Nordisk A/S, which is incorporated herein by reference as well as orally active hypoglycaemic agents.

The orally active hypoglycaemic agents preferably comprise sulphonylureas, biguanides, meglitinides, glucosidase inhibitors, glucagon antagonists such as those disclosed in WO 99/01423 to Novo Nordisk A/S and Agouron Pharmaceuticals, Inc., GLP-1 agonists, potassium channel openers such as those disclosed in WO 97/26265 and WO 99/03861 to Novo Nordisk A/S which are incorporated herein by reference, DPP-IV (dipeptidyl peptidase-IV) inhibitors, inhibitors of hepatic enzymes involved in stimulation of gluconeogenesis and/or glycogenolysis, glucose uptake modulators, compounds modifying the lipid metabolism such as antihyperlipidemic agents and antilipidemic agents as PPARα modulators, PPARδ modulators, cholesterol absorption inhibitors, HSL (hormone-sensitive lipase) inhibitors and HMG CoA inhibitors (statins), nicotinic acid, fibrates, anion exchangers, compounds lowering food intake, bile acid resins, RXR agonists and agents acting on the ATP-dependent potassium channel of the β-cells.

In one embodiment, the present compounds are administered in combination with insulin or an insulin analogue or derivative, such as $N^{\epsilon B29}$-tetradecanoyl des (B30) human insulin, $Asp^{B28}$ human insulin, $LyS^{B28}$ $Pro^{B29}$ human insulin, Lantus®, or a mix-preparation comprising one or more of these.

In a further embodiment the present compounds are administered in combination with a sulphonylurea e.g. tolbutamide, glibenclamide, glipizide or glicazide.

In another embodiment the present compounds are administered in combination with a biguanide e.g. metformin.

In yet another embodiment the present compounds are administered in combination with a meglitinide e.g. repaglinide or senaglinide.

In still another embodiment the present compounds are administered in combination with a thiazolidinedione e.g. troglitazone, ciglitazone, pioglitazone, rosiglitazone or compounds disclosed in WO 97/41097 such as 5-[[4-[3-Methyl-4-oxo-3,4-dihydro-2-quinazolinyl]methoxy]phenyl-methyl]thiazolidine-2,4-dione or a pharmaceutically acceptable salt thereof, preferably the potassium salt.

In yet another embodiment the present compounds may be administered in combination with the insulin sensitizers disclosed in WO 99/19313 such as (−)3-[4-[2-Phenoxazin-10-yl)ethoxy]phenyl]-2-ethoxypropanoic acid or a pharmaceutically acceptable salts thereof, preferably the arginine salt.

In a further embodiment the present compounds are administered in combination with an α-glucosidase inhibitor e.g. miglitol or acarbose.

In another embodiment the present compounds are administered in combination with an agent acting on the ATP-dependent potassium channel of the p-cells e.g. tolbutamide, glibenclamide, glipizide, glicazide or repaglinide.

Furthermore, the present compounds may be administered in combination with nateglinide.

In still another embodiment the present compounds are administered in combination with an antihyperlipidemic agent or antilipidemic agent e.g. cholestyramine, colestipol, clofibrate, gemfibrozil, fenofibrate, bezafibrate, tesaglitazar, EML-4156, LY-818, MK-767, atorvastatin, fluvastatin, lovastatin, pravastatin, simvastatin, acipimox, probucol, ezetimibe or dextrothyroxine.

In a further embodiment the present compounds are administered in combination with more than one of the above-mentioned compounds e.g. in combination with a sulphonylurea and metformin, a sulphonylurea and acarbose, repaglinide and metformin, insulin and a sulphonylurea, insulin and metformin, insulin, insulin and lovastatin, etc.

Further, the present compounds may be administered in combination with one or more antihypertensive agents. Examples of antihypertensive agents are β-blockers such as alprenolol, atenolol, timolol, pindolol, propranolol, metoprolol, bisoprololfumerate, esmolol, acebutelol, metoprolol, acebutolol, betaxolol, celiprolol, nebivolol, tertatolol, oxprenolol, amusolalul, carvedilol, labetalol, β2-receptor blockers e.g. S-atenolol, OPC-1085, ACE (angiotensin converting enzyme) inhibitors such as quinapril, lisinopril, enalapril, captopril, benazepril, perindopril, trandolapril, fosinopril, ramipril, cilazapril, delapril, imidapril, moexipril, spirapril, temocapril, zofenopril, S-5590, fasidotril, Hoechst-Marion Roussel: 100240 (EP 00481522), omapatrilat, gemopatrilat and GW-660511, calcium channel blockers such as nifedipine, felodipine, nicardipine, isradipine, nimodipine, diltiazem, amlodipine, nitrendipine, verapamil, lacidipine, lercanidipine, aranidipine, cilnidipine, clevidipine, azelnidipine, barnidipine, efonodipine, iasidipine, iemildipine, iercanidipine, manidipine, nilvadipine, pranidipine, furnidipine, α-blockers such as doxazosin, urapidil, prazosin, terazosin, bunazosin and OPC-28326, diuretics such as thiazides/sulphonamides (e.g. bendroflumetazide, chlorothalidone, hydrochlorothiazide and clopamide), loop-diuretics (e.g. bumetanide, furosemide and torasemide) and potassium sparing diuretics (e.g. amiloride, spironolactone), endothelin ET-A antagonists such as ABT-546, ambrisetan, atrasentan, SB-234551, Cl-1034, S-0139 and YM-598, endothelin antagonists e.g. bosentan and J-104133, renin inhibitors such as aliskiren, vasopressin V1 antagonists e.g. OPC-21268, vasopressin V2 antagonists such as tolvaptan, SR-121463 and OPC-31260, B-type natriuretic peptide agonists e.g. Nesiritide, angiotensin II antagonists such as irbesartan, candesartancilexetil, losartan, valsartan, telmisartan, eprosartan, candesartan, CL-329167, eprosartan, iosartan, olmesartan, pratosartan, TA-606, and YM-358, 5-HT2 agonists e.g. fenoldopam and ketanserin, adenosine A1 antagonists such as naftopidil, N-0861 and FK-352, thromboxane A2 antagonists such as KT2-962, endopeptidase inhibitors e.g. ecadotril, nitric oxide agonists such as LP-805, dopamine D1 antagonists e.g. MYD-37, dopamine D2 agonists such as nolomirole, n-3 fatty acids e.g. omacor, prostacyclin agonists such as treprostinil, beraprost, PGE1 agonists e.g. ecraprost, Na+/K+ ATPase modulators e.g. PST-2238, Potassium channel activators e.g. KR-30450, vaccines such as PMD-3117, Indapamides, CGRP-unigene, guanylate cyclase stimulators, hydralazines, methyldopa, docarpamine, moxonidine, CoAprovel, MondoBiotech-811.

Further reference can be made to Remington: The Science and Practice of Pharmacy, 19$^{th}$ Edition, Gennaro, Ed., Mack Publishing Co., Easton, Pa., 1995.

Furthermore, the present compounds may be administered in combination with one or more glucocorticoid receptor agonists. Examples of such glucocorticoid receptor agonists are betametasone, dexamethasone, hydrocortisone, methylprednisolone, prednisolone, prednisone, beclomethasone, butixicort, clobetasol, flunisolide, flucatisone (and analogues), mometasone, triamcinolonacetonide, triamcinolonhexacetonide GW-685698, NXC-1015, NXC-1020, NXC-1021, NS-126, P-4112, P-4114, RU-24858 and T-25 series.

It should be understood that any suitable combination of the compounds according to the invention with one or more of the above-mentioned compounds and optionally one or more further pharmacologically active substances are considered to be within the scope of the present invention.

PHARMACEUTICAL COMPOSITIONS

The compounds of the present invention may be administered alone or in combination with pharmaceutically acceptable carriers or excipients, in either single or multiple doses. The pharmaceutical compositions according to the invention may be formulated with pharmaceutically acceptable carriers or diluents as well as any other known adjuvants and excipients in accordance with conventional techniques such as those disclosed in Remington: The Science and Practice of Pharmacy, 19$^{th}$ Edition, Gennaro, Ed., Mack Publishing Co., Easton, Pa., 1995.

The pharmaceutical compositions may be specifically formulated for administration by any suitable route such as the oral, rectal, nasal, pulmonary, topical (including buccal and sublingual), transdermal, intracisternal, intraperitoneal, vaginal and parenteral (including subcutaneous, intramuscular, intrathecal, intravenous and intradermal) route, the oral route being preferred. It will be appreciated that the preferred route will depend on the general condition and age of the subject to be treated, the nature of the condition to be treated and the active ingredient chosen.

Pharmaceutical compositions for oral administration include solid dosage forms such as hard or soft capsules, tablets, troches, dragees, pills, lozenges, powders and granules. Where appropriate, they can be prepared with coatings such as enteric coatings or they can be formulated so as to provide controlled release of the active ingredient such as sustained or prolonged release according to methods well-known in the art.

Liquid dosage forms for oral administration include solutions, emulsions, suspensions, syrups and elixirs.

Pharmaceutical compositions for parenteral administration include sterile aqueous and non-aqueous injectable solutions, dispersions, suspensions or emulsions as well as sterile powders to be reconstituted in sterile injectable solutions or dispersions prior to use. Depot injectable formulations are also contemplated as being within the scope of the present invention.

Other suitable administration forms include suppositories, sprays, ointments, crèmes, gels, inhalants, dermal patches, implants etc.

A typical oral dosage is in the range of from about 0.001 to about 100 mg/kg body weight per day, preferably from about 0.01 to about 50 mg/kg body weight per day, and more preferred from about 0.05 to about 10 mg/kg body weight per day administered in one or more dosages such as 1 to 3 dosages. The exact dosage will depend upon the frequency and mode of administration, the sex, age, weight and general condition of the subject treated, the nature and severity of the condition treated and any concomitant diseases to be treated and other factors evident to those skilled in the art.

The formulations may conveniently be presented in unit dosage form by methods known to those skilled in the art. A typical unit dosage form for oral administration one or more times per day such as 1 to 3 times per day may contain from 0.05 to about 2000 mg, e.g. from about 0.1 to about 1000 mg, from about 0.5 mg to about 500 mg., from about 1 mg to about 200 mg, e.g. about 100 mg.

For parenteral routes, such as intravenous, intrathecal, intramuscular and similar administration, typically doses are in the order of about half the dose employed for oral administration.

The compounds of this invention are generally utilized as the free substance or as a pharmaceutically acceptable salt thereof. Examples are an acid addition salt of a compound having the utility of a free base and a base addition salt of a compound having the utility of a free acid. The term "pharmaceutically acceptable salts" refers to non-toxic salts of the compounds for use according to the present invention which are generally prepared by reacting the free base with a suitable organic or inorganic acid or by reacting the acid with a suitable organic or inorganic base. When a compound for use according to the present invention, contains a free base such salts are prepared in a conventional manner by treating a solution or suspension of the compound with a chemical equivalent of a pharmaceutically acceptable acid. When a compounds for use according to the present invention, contains a free acid such salts are prepared in a conventional manner by treating a solution or suspension of the compound with a chemical equivalent of a pharmaceutically acceptable base. Physiologically acceptable salts of a compound with a hydroxy group include the anion of said compound in combination with a suitable cation such as sodium or ammonium ion. Other salts which are not pharmaceutically acceptable may be useful in the preparation of compounds for use according to the present invention and these form a further aspect of the present invention.

For parenteral administration, solutions of the present compounds in sterile aqueous solution, aqueous propylene glycol or sesame or peanut oil may be employed. Such aqueous solutions should be suitable buffered if necessary and the liquid diluent first rendered isotonic with sufficient saline or glucose. The aqueous solutions are particularly suitable for intravenous, intramuscular, subcutaneous and intraperitoneal administration. The sterile aqueous media employed are all readily available by standard techniques known to those skilled in the art.

Suitable pharmaceutical carriers include inert solid diluents or fillers, sterile aqueous solution and various organic solvents. Examples of suitable carriers are water, salt solutions, alcohols, polyethylene glycols, polyhydroxyethoxylated castor oil, peanut oil, olive oil, syrup, phospholipids, gelatine, lactose, terra alba, sucrose, cyclodextrin, amylose, magnesium stearate, talc, gelatin, agar, pectin, acacia, stearic acid or lower alkyl ethers of cellulose, silicic acid, fatty acids, fatty acid amines, fatty acid monoglycerides and diglycerides, pentaerythritol fatty acid esters, polyoxyethylene, hydroxymethylcellulose and polyvinylpyrrolidone. Similarly, the carrier or diluent may include any sustained release material known in the art, such as glyceryl monostearate or glyceryl distearate, alone or mixed with a wax. The formulations may also include wetting agents, emulsifying and suspending agents, preserving agents, sweetening agents or flavouring agents.

The pharmaceutical compositions formed by combining the compounds of the invention and the pharmaceutically acceptable carriers are then readily administered in a variety of dosage forms suitable for the disclosed routes of administration. The formulations may conveniently be presented in unit dosage form by methods known in the art of pharmacy.

Formulations of the present invention suitable for oral administration may be presented as discrete units such as capsules or tablets, each containing a predetermined amount of the active ingredient, and which may include a suitable excipient. These formulations may be in the form of powder or granules, as a solution or suspension in an aqueous or non-aqueous liquid, or as an oil-in-water or water-in-oil liquid emulsion.

Compositions intended for oral use may be prepared according to any known method, and such compositions may contain one or more agents selected from the group consisting of sweetening agents, flavouring agents, colouring agents, and preserving agents in order to provide pharmaceutically elegant and palatable preparations. Tablets may contain the active ingredient in admixture with non-toxic pharmaceutically-acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example corn starch or alginic acid; binding agents, for example, starch, gelatine or acacia; and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in U.S. Pat. Nos. 4,356,108; 4,166,452; and 4,265,874, incorporated herein by reference, to form osmotic therapeutic tablets for controlled release.

Formulations for oral use may also be presented as hard gelatine capsules where the active ingredient is mixed with an inert solid diluent, for example, calcium carbonate, calcium phosphate or kaolin, or a soft gelatine capsule wherein the active ingredient is mixed with water or an oil medium, for example peanut oil, liquid paraffin, or olive oil.

Aqueous suspensions may contain the active compounds in admixture with excipients suitable for the manufacture of aqueous suspensions. Such excipients are suspending agents, for example sodium carboxymethylcellulose, methylcellulose, hydroxypropylmethylcellulose, sodium alginate, polyvinylpyrrolidone, gum tragacanth and gum acacia; dispersing or wetting agents may be a naturally-occurring phosphatide such as lecithin, or condensation products of an alkylene oxide with fatty acids, for example polyoxyethylene stearate, or condensation products of ethylene oxide with long chain aliphatic alcohols, for example, heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more colouring agents, one or more flavouring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as a liquid paraffin. The oily suspensions may contain a thickening agent, for example beeswax, hard paraffin or cetyl alcohol. Sweetening agents such as those set forth above, and flavouring agents may be added to provide a palatable oral preparation. These compositions may be pre-served by the addition of an anti-oxidant such as ascorbic acid.

Dispersible powders and granules suitable for preparation of an aqueous suspension by the addition of water provide the active compound in admixture with a dispersing or wetting agent, suspending agent and one or more preservatives. Suitable dispersing or wetting agents and suspending agents are exemplified by those already mentioned above. Additional excipients, for example, sweetening, flavouring, and colouring agents may also be present.

The pharmaceutical compositions comprising a compound for use according to the present invention may also be in the form of oil-in-water emulsions. The oily phase may be a vegetable oil, for example, olive oil or arachis oil, or a mineral oil, for example a liquid paraffin, or a mixture thereof. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of said partial esters with ethylene oxide, for example polyoxyethylene sorbitan monooleate. The emulsions may also contain sweetening and flavouring agents.

Syrups and elixirs may be formulated with sweetening agents, for example glycerol, propylene glycol, sorbitol or sucrose. Such formulations may also contain a demulcent, preservative and flavouring and colouring agent. The pharmaceutical compositions may be in the form of a sterile injectable aqueous or oleaginous suspension. This suspension may be formulated according to the known methods using suitable dispersing or wetting agents and suspending agents described above. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution, and isotonic sodium chloride solution. In addition, sterile, fixed oils are conveniently employed as solvent or suspending medium. For this purpose, any bland fixed oil may be employed using synthetic mono- or diglycerides. In addition, fatty acids such as oleic acid find use in the preparation of injectables.

The compositions may also be in the form of suppositories for rectal administration of the compounds of the present invention. These compositions can be prepared by mixing the drug with a suitable non-irritating excipient which is solid at ordinary temperatures but liquid at the rectal temperature and will thus melt in the rectum to release the drug. Such materials include cocoa butter and polyethylene glycols, for example.

For topical use, creams, ointments, jellies, solutions of suspensions, etc., containing the compounds of the present invention are contemplated. For the purpose of this application, topical applications shall include mouth washes and gargles.

The compounds for use according to the present invention may also be administered in the form of liposome delivery systems, such as small unilamellar vesicles, large unilamellar vesicles, and multilamellar vesicles. Liposomes may be formed from a variety of phospholipids, such as cholesterol, stearylamine, or phosphatidylcholines.

In addition, some of the compounds for use according to the present invention may form solvates with water or common organic solvents. Such solvates are also encompassed within the scope of the present invention.

Thus, in a further embodiment, there is provided a pharmaceutical composition comprising a compound for use according to the present invention, or a pharmaceutically acceptable salt, solvate, or prodrug thereof, and one or more pharmaceutically acceptable carriers, excipients, or diluents.

If a solid carrier is used for oral administration, the preparation may be tabletted, placed in a hard gelatine capsule in powder or pellet form or it can be in the form of a troche or lozenge. The amount of solid carrier will vary widely but will usually be from about 25 mg to about 1 g. If a liquid carrier is used, the preparation may be in the form of a syrup, emulsion, soft gelatine capsule or sterile injectable liquid such as an aqueous or non-aqueous liquid suspension or solution.

A typical tablet which may be prepared by conventional tabletting techniques may contain:

| Core: | |
|---|---|
| Active compound (as free compound or salt thereof) | 5.0 mg |
| Lactosum Ph. Eur. | 67.8 mg |
| Cellulose, microcryst. (Avicel) | 31.4 mg |
| Amberlite ® IRP88* | 1.0 mg |
| Magnesii stearas Ph. Eur. | q.s. |
| Coating: | |
| Hydroxypropyl methylcellulose | approx. 9 mg |
| Mywacett 9-40 T** | approx. 0.9 mg |

*Polacrillin potassium NF, tablet disintegrant, Rohm and Haas.
**Acylated monoglyceride used as plasticizer for film coating.

The compounds of the invention may be administered to a patient which is a mammal, especially a human in need thereof. Such mammals include also animals, both domestic animals, e.g. household pets, and non-domestic animals such as wildlife.

Any novel feature or combination of features described herein is considered essential to this invention.

The present invention also relate to the below methods of preparing the compounds of the invention.

The present invention is further illustrated in the following representative examples which are, however, not intended to limit the scope of the invention in any way.

EXAMPLES

The following examples and general procedures refer to intermediate compounds and final products for general formula (I) identified in the specification and in the synthesis schemes. The preparation of the compounds of general formula (I) of the present invention is described in detail using the following examples. Occasionally, the reaction may not be applicable as described to each compound included within the disclosed scope of the invention. The compounds for which this occurs will be readily recognised by those skilled in the art. In these cases the reactions can be successfully performed by conventional modifications known to those skilled in the art, which is, by appropriate protection of interfering groups, by changing to other conventional reagents, or by routine modification of reaction conditions. Alternatively, other reactions disclosed herein or otherwise conventional will be applicable to the preparation of the corresponding compounds of the invention. In all preparative methods, all starting materials are known or may easily be prepared from known starting materials. The structures of the compounds are confirmed by either elemental analysis or nuclear magnetic resonance (NMR), where peaks assigned to characteristic protons in the title compounds are presented where appropriate. $^1$H NMR shifts ($\delta_H$) are given in parts per million (ppm) down field from tetramethylsilane as internal reference standard. M.p.: is melting point and is given in ° C. and is not corrected. Column chromatography was carried out using the technique described by W. C. Still et al., *J. Org. Chem.* 43:2923 (1978) on Merck silica gel 60 (Art. 9385). HPLC analyses are performed using 5 μm C18 4×250 mm column eluted with various mixtures of water and acetonitrile, flow=1 ml/min, as described in the experimental section.

Microwave oven synthesis: The reaction was heated by microwave irradiation in sealed microwave vessels in a single mode Emrys Optimizer EXP from PersonalChemistry®.

Preparative HPLC: Column: 1.9×15 cm Waters XTerra RP-18. Buffer: linear gradient 5-95% in 15 min, MeCN, 0.1% TFA, flow rate of 15 ml/min. The pooled fractions are either evaporated to dryness in vacuo, or evaporated in vacuo until the MeCN is removed, and then frozen and freeze dried.

The abbreviations as used in the examples have the following meaning:
TLC: Thin layer chromatography
CDCl$_3$: Deuterio chloroform
DCM: Dichloromethane
DIIC: N,N'-Diisopropylcarbodiimide
DMAP: 4-Dimethylaminopyridine
DMSO-d$_6$: Hexadeuterio dimethylsulfoxide
DMSO: Dimethylsulfoxide
DIPEA: Diisopropylethylamine
EDAC: 1-(3-Dimethylaminopropyl)-3-ethylcarbodiimide hydrochloride
EtOAc: Ethyl acetate
THF: Tetrahydrofuran
DMF: N,N-dimethylformamide
HOBT: 1-Hydroxy-benzotriazole
POL: Polystyrene
MeCN: Acetonitrile
NMP: N-Methylpyrrolidinone
TEA: Triethylamine
TFA: Trifluoroacetic acid
EDAC: 1-(3-Dimethylaminopropyl)-3-ethylcarbodiimide, hydrochloride
min: minutes
hrs: hours General Method A By allowing an acid (I) wherein $R^1$, $R^2$ and $R^{16}$ are defined as above to be coupled with an amine (II) wherein l, m, W, Q, X, Y and Z are defined as above under standard amide forming conditions using a coupling reagent (III) (e.g. HOBT, EDAC and DIPEA in dry THF) affording amide (IV) wherein $R^1$, $R^2$, $R^{16}$, l, m, W, Q, X, Y and Z are defined as above.

General Method B

By allowing an acid (I) wherein $R^1$, $R^2$ and $R^{16}$ are defined as above to react with HOBt-6-carboxamidomethyl polystyrene (II) followed by amine (III) wherein l, m, W, Q, X, Y and Z are defined as above under standard solid-phase amide forming conditions using a coupling reagent (IV) (e.g. DIIC and DIPEA in DMF/1,2-dichloropropane) affording amide (V) wherein $R^1$, $R^2$, $R^{16}$, l, m, W, Q, X, Y and Z are defined as above.

Example 1

8-(1H-Indole-5-carbonyl)-1-phenyl-1,3,8-triaza-spiro[4.5]decan-4-one

To a mixture of indole-5-carboxylic acid (300 mg, 1.86 mmol) and HOBT (278 mg, 2.05 mmol) in dry DMF (10 mL) was added EDAC (464 mg, 2.42 mmol). The resulting mixture was stirred for 10 min followed by addition of a mixture of TEA (0.78 ml, 5.58 mmol) and 1-phenyl-1,3,8-triaza-spiro [4.5]decan-4-one (473 mg, 2.04 mmol). The reaction mixture was stirred for an additional 16 hrs. To the reaction mixture was added water (25 ml) and the resulting precipitate was filtered and washed with water. The resulting solid was recrystalised from a mixture of EtOH-water (4:1, 10 mL) the precipitate was filtered off, washed with water and dried in vacuo at 40° C. affording 472 mg (67%) of the title compound as a solid.

MS-ESI m/z 375; $^1$H-NMR (300 MHz, DMSO-d$_6$) δ 1.58-1.73 (m, 2H), 2.39-2.69 (m, 4H), 3.54-3.73 (m, 2H), 4.61 (s, 2H), 6.49 (m, 1H), 6.75-6.82 (m, 3H), 7.16-7.21 (d, 2H), 7.25-7.32 (m, 2H), 7.39-7.48 (m, 2H), 7.68 (s, 1H), 8.80 (s, 1H), 11.29 (s, 1H).

Example 2

3,4-Dihydrospiro(1H-indene-1,4'-piperidin-1-yl)-(1H-indol-5-yl)-methanone

To HOBt-6-carboxamidomethyl polystyrene (100 mg, 0.1 mmol) pre-swollen in DCM was added a solution of indole-5-carboxylic acid (24 mg, 0.15 mmol) in DMF (0.25 mL) followed by a solution of DMAP (7 mg, 0.006 mmol) in DCM (0.75 mL). The mixture was shaken for 10 min before the addition of DIIC (0.072 mL, 0.44 mmol) in DCM (0.25 mL) and the resulting mixture shaken for a further 5 hrs before the excess reagents were removed by filtration. After the resin had been washed with DCM (10×1.5 mL) a solution of 3,4-Dihydrospiro(1H-indene-1,4'-piperidine) hydrochloride (19 mg, 0.085 mmol) in 1,2-dichloroethane (1.2 mL) and DIPEA (0.03 mL, 0.17 mmol) was added. The resulting mixture was shaken for 16 hrs before the product solution was removed by filtration and the resin washed with DCM:MeOH (3:1, v/v, 1 mL). The combined filtrates were concentrated in vacuo and the residue was purified by preparative HPLC, dried in vacuo at 50° C. affording 18 mg (64%) of the title compound as a white solid.

MS-ESI m/z 331; $^1$H NMR (400 MHz, CDCl$_3$) δ 1.45-1.70 (m, 2H), 1.80-2.02 (m, 2H), 2.08-2.17 (m, 2H), 2.90-2.97 (m, 2H), 3.04-3.29 (m, 2H), 3.85-4.09 (m, 1H), 4.60-4.89 (m, 1H), 6.59 (s, 1H), 7.13-7.29 (m, 5H), 7.30-7.34 (m, 1H), 7.39-7.42 (m, 1H), 7.78 (s, 1H), 8.42 (s, 1H).

The following compounds were synthesised employing a similar method to the ones described in examples 1, and 2 above:

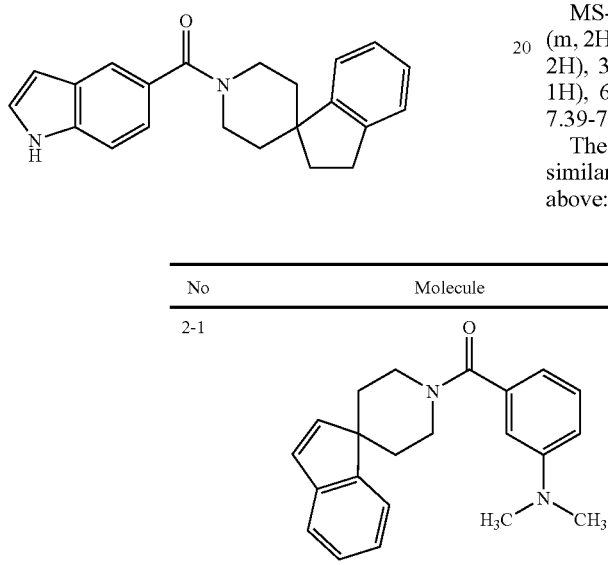

| No | Molecule | IUPAC Name |
|---|---|---|
| 2-1 | | Spiro(1H-indene-1,4'-piperidin-1-yl)-(3-N,N-dimethylamino-phenyl)-methanone |
| 2-2 | | Spiro(1H-indene-1,4'-piperidin-1-yl)-(1H-benzimidazol-5-yl)-methanone |
| 2-3 | | 2,3-Dihydrospiro(1-methanesulfonyl-indol-3,4'-piperidin-1-yl)-(1H-indol-5-yl)-methanone |

-continued

| No | Molecule | IUPAC Name |
|---|---|---|
| 2-4 | | 2,3-Dihydrospiro(1-methanesulfonyl-indol-3,4'-piperidin-1-yl)-(3-N,N-dimethylamino-phenyl)-methanone |
| 2-5 | | Spiro(1H-indene-1,4'-piperidin-1-yl)-(4-(2,4-dihydro-5-methyl-pyrazol-2-yl-3-one)phenyl)-methanone |
| 2-6 | | Spiro(1H-indene-1,4'-piperidin-1-yl)-(4-(imidazole-1-yl)phenyl)-methanone |
| 2-7 | | Spiro(cyclopentane-1,4'-piperidin-1-yl)-(1H-benzimidazol-5-yl)-methanone |
| 2-8 | | 2,3-Dihydrospiro(1H-indene-1,4'-piperidin-1-yl)-(4-N,N-dimethylamino-phenyl)-methanone |
| 2-9 | | Spiro(1H-indene-1,4'-piperidin-1-yl)-(4-N,N-dimethylamino-phenyl)-methanone |

-continued

| No | Molecule | IUPAC Name |
|---|---|---|
| 2-10 | | 2,3-Dihydrospiro(1H-indene-1,4'-piperidin-1-yl)-(1H-benzimidazol-5-yl)-methanone |
| 2-11 | | 2,3-Dihydrospiro(1-methanesulfonyl-indol-3,4'-piperidin-1-yl)-(benzimidazol-5-yl)-methanone |
| 2-12 | | 1,3-Dihydrospiro(1H-indene-2,4'-piperidin-1-yl)-(4-N,N-dimethylamino-phenyl)-methanone |
| 2-13 | | Spiro(1-tert-butyl-pyrrolidin-2-one-3,4'-piperidin-1-yl)-(4-N,N-dimethylamino-phenyl)-methanone |

Pharmacological Methods

11βHSD1 Enzyme Assay

Materials $^3$H-cortisone and anti-rabbit Ig coated scintillation proximity assay (SPA) beads were purchased from Amersham Pharmacia Biotech, β-NADPH was from Sigma and rabbit anti-cortisol antibodies were from Fitzgerald. An extract of yeast transformed with h-11βHSD1 (Hult et al., *FEBS Lett*, 441, 25 (1998)) was used as the source of enzyme. The test compounds were dissolved in DMSO (10 mM). All dilutions were performed in a buffer containing 50 mM TRIS-HCl (Sigma Chemical Co), 4 mM EDTA (Sigma Chemical Co), 0.1% BSA (Sigma Chemical Co), 0.01% Tween-20 (Sigma Chemical Co) and 0.005% bacitracin (Novo Nordisk A/S), pH=7.4. Optiplate 96 wells plates were supplied by Packard. The amount of $^3$H-cortisol bound to the SPA beads was measured on TopCount NXT, Packard.

Methods h-11βHSD1, 120 nM $^3$H-cortisone, 4 mM β-NADPH, antibody (1:200), serial dilutions of test compound and SPA particles (2 mg/well) were added to the wells. The reaction was initiated by mixing the different components and was allowed to proceed under shaking for 60 min at 30° C. The reaction was stopped be the addition of 10 fold excess of a stopping buffer containing 500 μM carbenoxolone and 1 μM cortisone. Data was analysed using GraphPad Prism software.

The invention claimed is:

1. A compound selected from the group consisting of:

2,3-Dihydrospiro(1-methanesulfonyl-indol-3,4'-piperidin-1-yl)-(1H-indol-5-yl)-methanone;

2,3-Dihydrospiro(1-methanesulfonyl-indol-3,4'-piperidin-1-yl)-(3-N,N-dimethylamino-phenyl)-methanone; and 2,3-Dihydrospiro(1-methanesulfonyl-indol-3,4'-piperidin-1-yl)-(benzimidazol-5-yl)-methanone; or a pharmaceutically acceptable salt thereof.

2. A pharmaceutical composition comprising a compound of claim 1 and a pharmaceutically acceptable carrier or excipient.

* * * * *